United States Patent
Salo et al.

(10) Patent No.: US 6,708,061 B2
(45) Date of Patent: Mar. 16, 2004

(54) CARDIAC RHYTHM MANAGEMENT SYSTEM WITH OPTIMIZATION OF CARDIAC PERFORMANCE USING HEART RATE

(75) Inventors: Rodney W. Salo, Fridley, MN (US); Kenneth L. Baker, Shoreview, MN (US); Lawrence S. Baumann, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 599 days.

(21) Appl. No.: 09/734,282

(22) Filed: Dec. 11, 2000

(65) Prior Publication Data

US 2001/0031993 A1 Oct. 18, 2001

Related U.S. Application Data

(63) Continuation-in-part of application No. 09/545,536, filed on Apr. 7, 2000.

(51) Int. Cl.[7] .................................................. A61N 1/18
(52) U.S. Cl. ................................ 607/9; 607/15; 607/25; 607/27
(58) Field of Search ............................ 607/9, 25, 27, 607/15, 123

(56) References Cited

U.S. PATENT DOCUMENTS

| 4,674,518 A | 6/1987 | Salo |
|---|---|---|
| 4,686,987 A | 8/1987 | Salo et al. |
| 4,733,667 A | 3/1988 | Olive et al. |
| 5,179,949 A | 1/1993 | Chirife |
| 5,312,452 A | 5/1994 | Salo |
| 5,330,511 A | 7/1994 | Boute |
| 5,334,222 A | 8/1994 | Salo et al. |
| 5,466,245 A | 11/1995 | Spinelli et al. |
| 5,487,752 A | 1/1996 | Salo et al. |
| 5,540,727 A | 7/1996 | Tockman et al. |
| 5,713,930 A | 2/1998 | van der Veen et al. |
| 5,716,383 A | 2/1998 | Kieval et al. |
| 5,792,203 A | 8/1998 | Schroeppel |
| 5,800,465 A | 9/1998 | Thompson et al. |
| 5,800,471 A | 9/1998 | Baumann |
| 6,044,298 A | 3/2000 | Salo et al. |

OTHER PUBLICATIONS

"Usefulness of Physiologic Dual–Chamber Pacing in Drug–Resistant Idiopathic Dilated Cardiomyopathy", *The American Journal of Cardiology*, Hochleitner, Hortnagl, Choi–Keung Ng, et al., vol. 66, Jul. 15, 1990, pp. 198–202.

"Hemodynamic Effect of Physiological Dual Chamber Pacing in a Patient with End–Stage Dilated Cardiomyopathy: A Case Report", Hajime Kataoka, PACE, Vol. 14, Sep. 1991, pp. 1330–1335.

*Primary Examiner*—Mark Bockelman
(74) *Attorney, Agent, or Firm*—Nikolai & Mersereau, PA; C. G. Mersereau

(57) ABSTRACT

A cardiac rhythm management device includes a dual chamber pacemaker, especially designed for treating congestive heart failure by pacing a plurality of sites. The device incorporates a program microcontroller which is operative to adjust the pacing mode and inter-site delay of the pacemaker so as to achieve optimum hemodynamic performance. Atrial cycle lengths measured during transient (immediate) time intervals following a change in the mode inter-site delay are signal processed and a determination can then be made as to which particular configuration yields the optimum performance. Performance is optimized when the patient is at rest and when the patient exercises so that a rate-adapted dynamic value of the optimum performance can be applied.

21 Claims, 20 Drawing Sheets

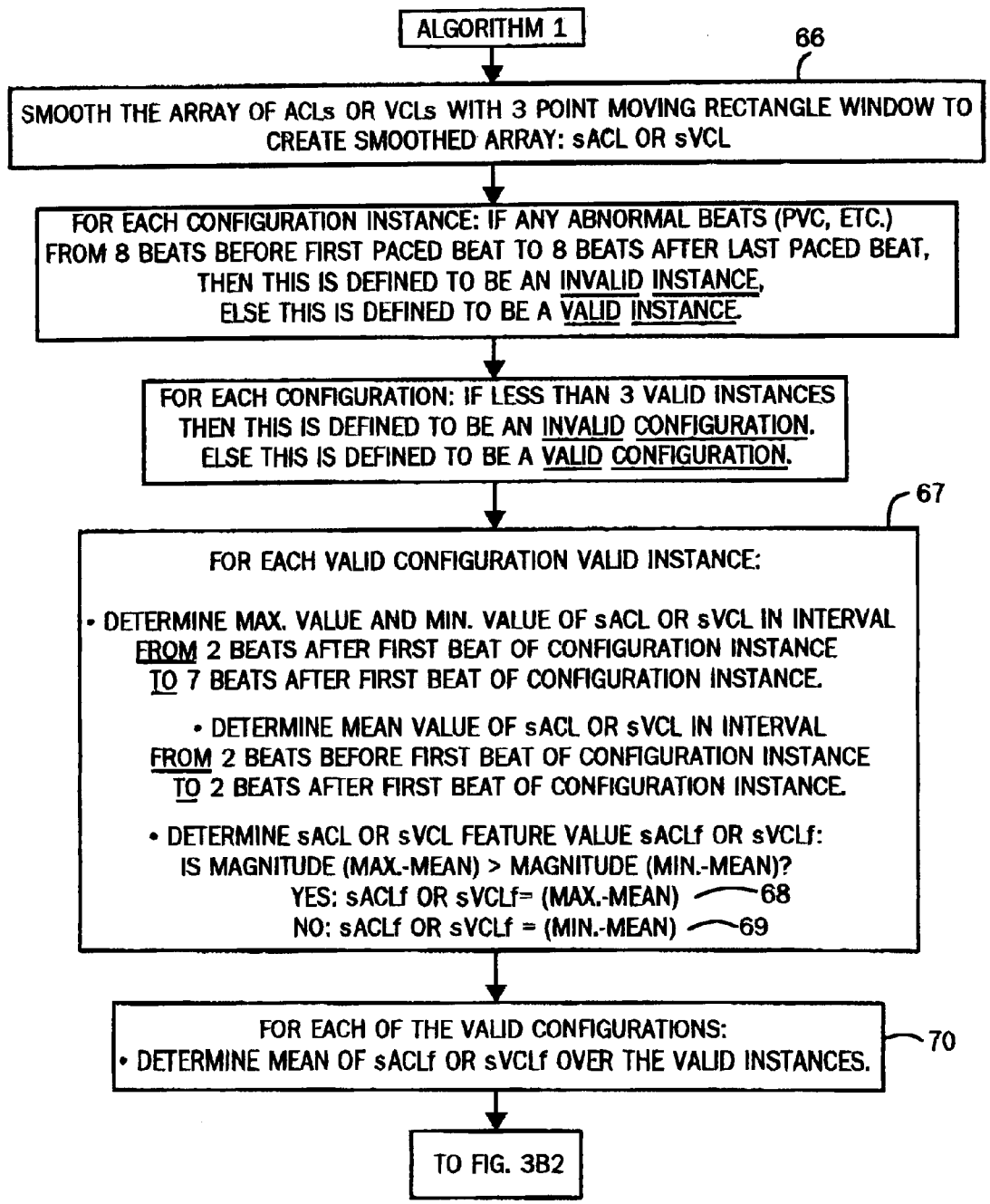
FIG. 3B1

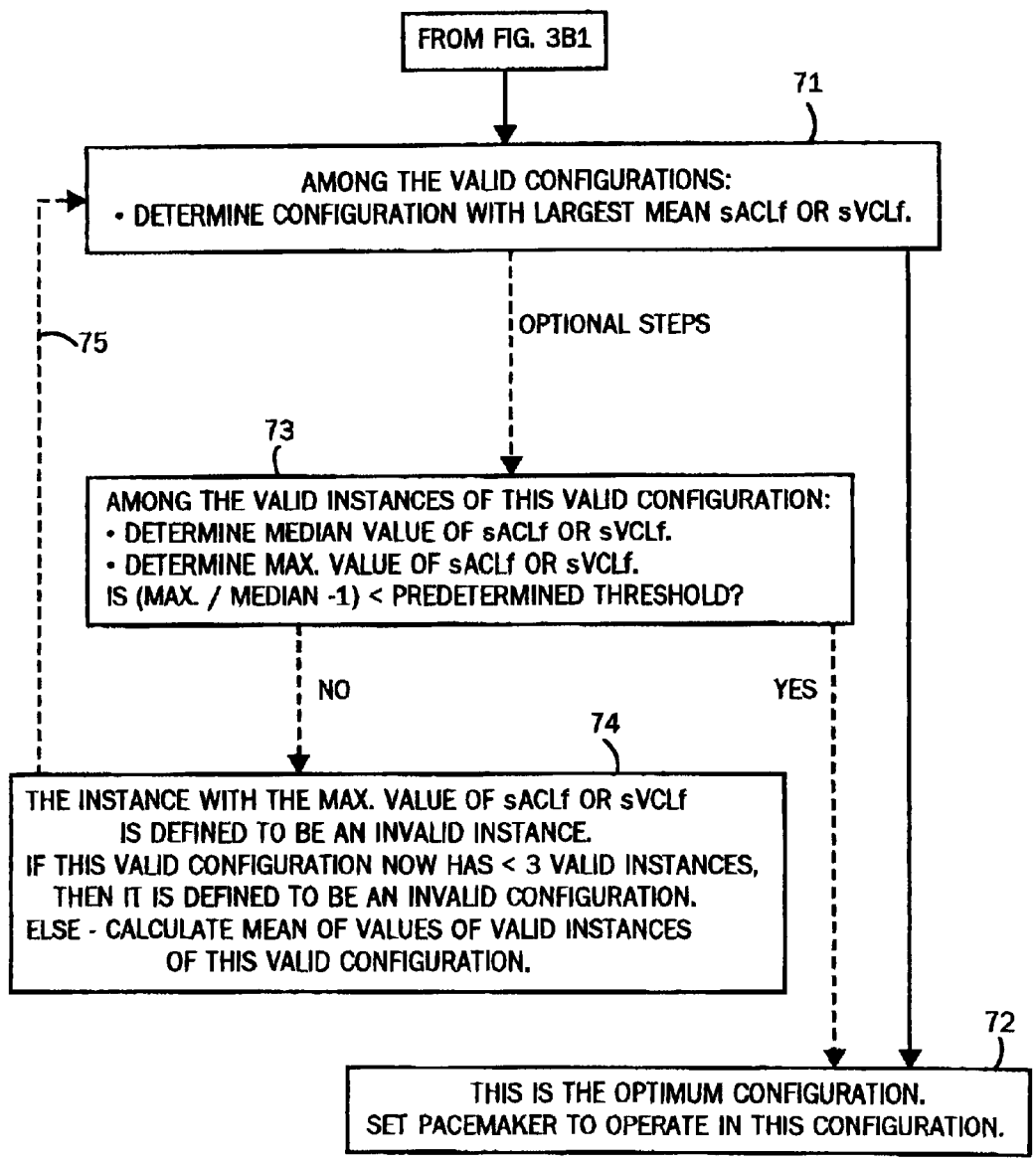
FIG. 3B2

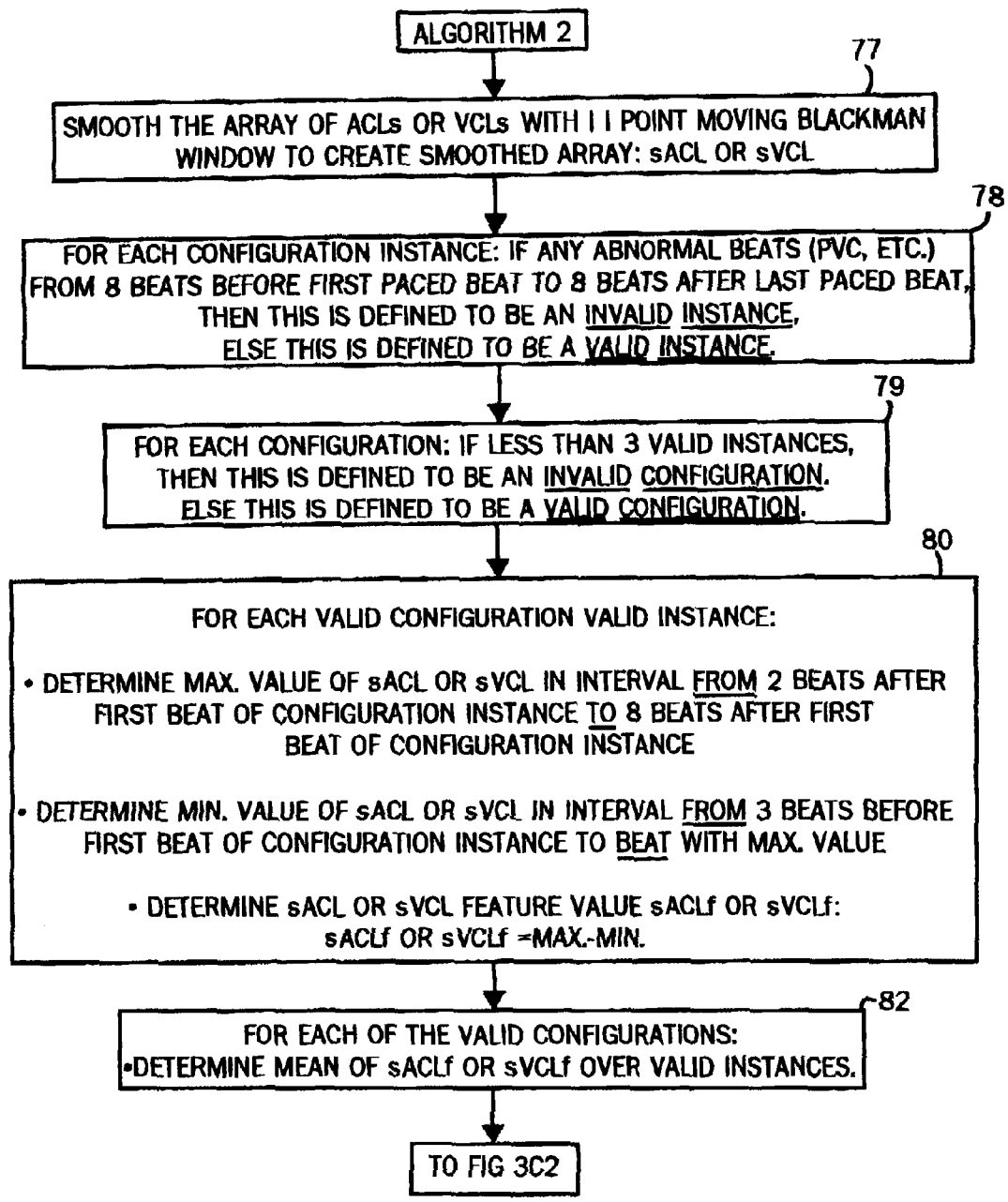
FIG. 3C1

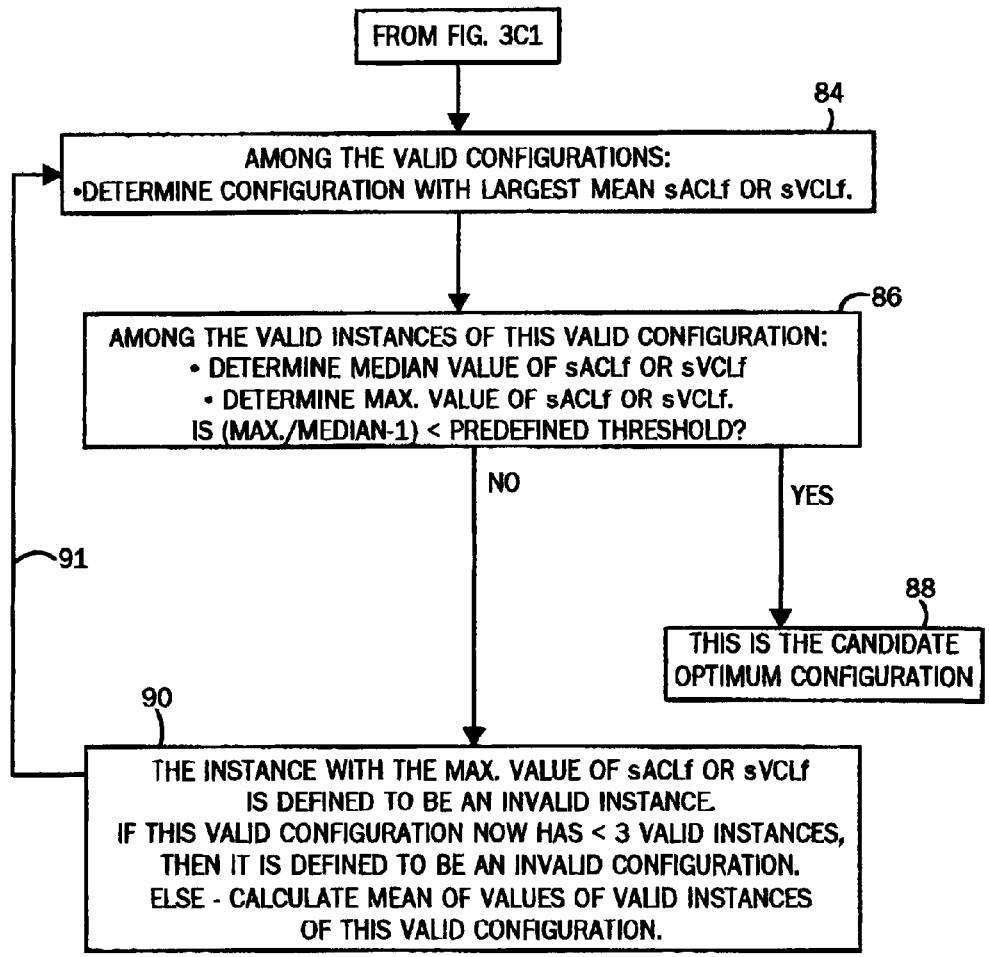
FIG. 3C2

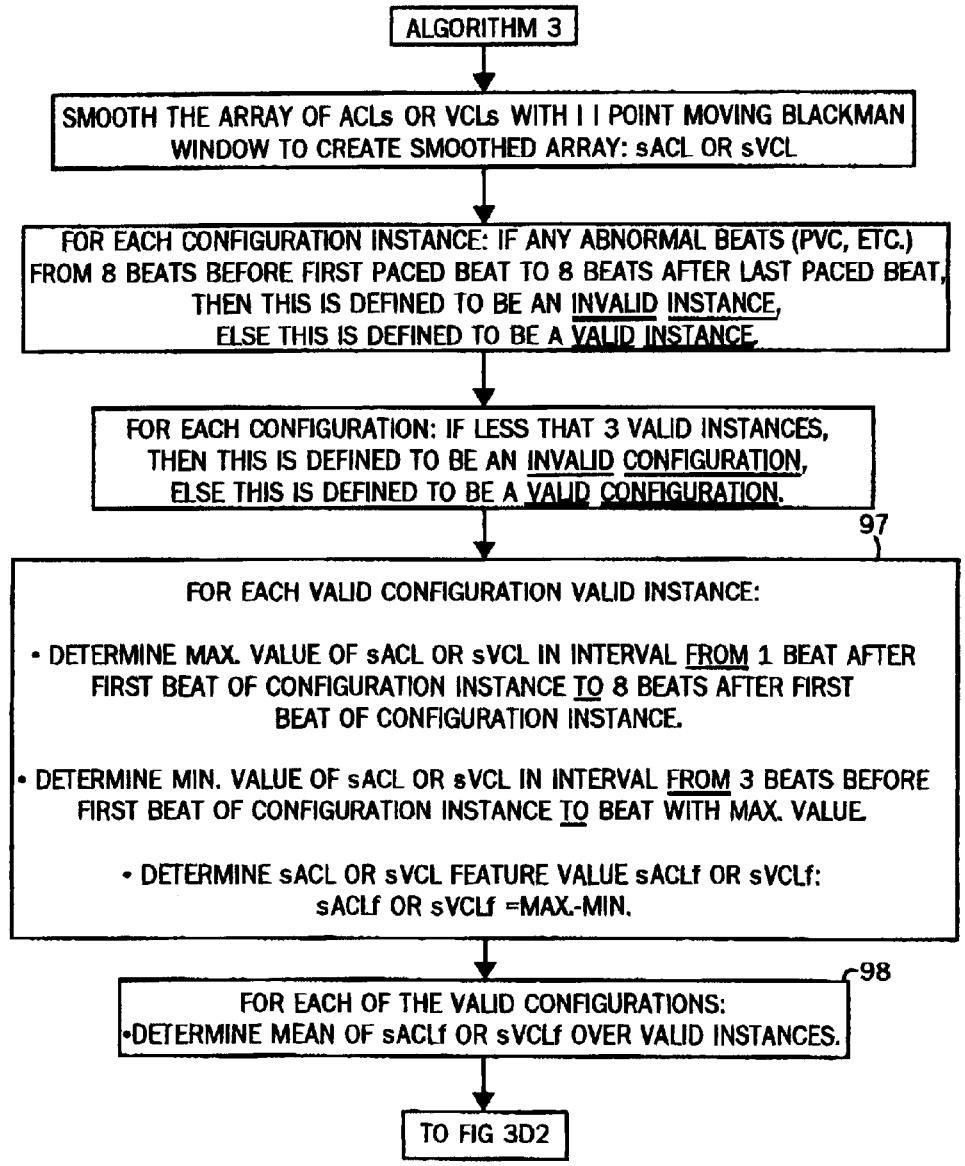
FIG. 3D1

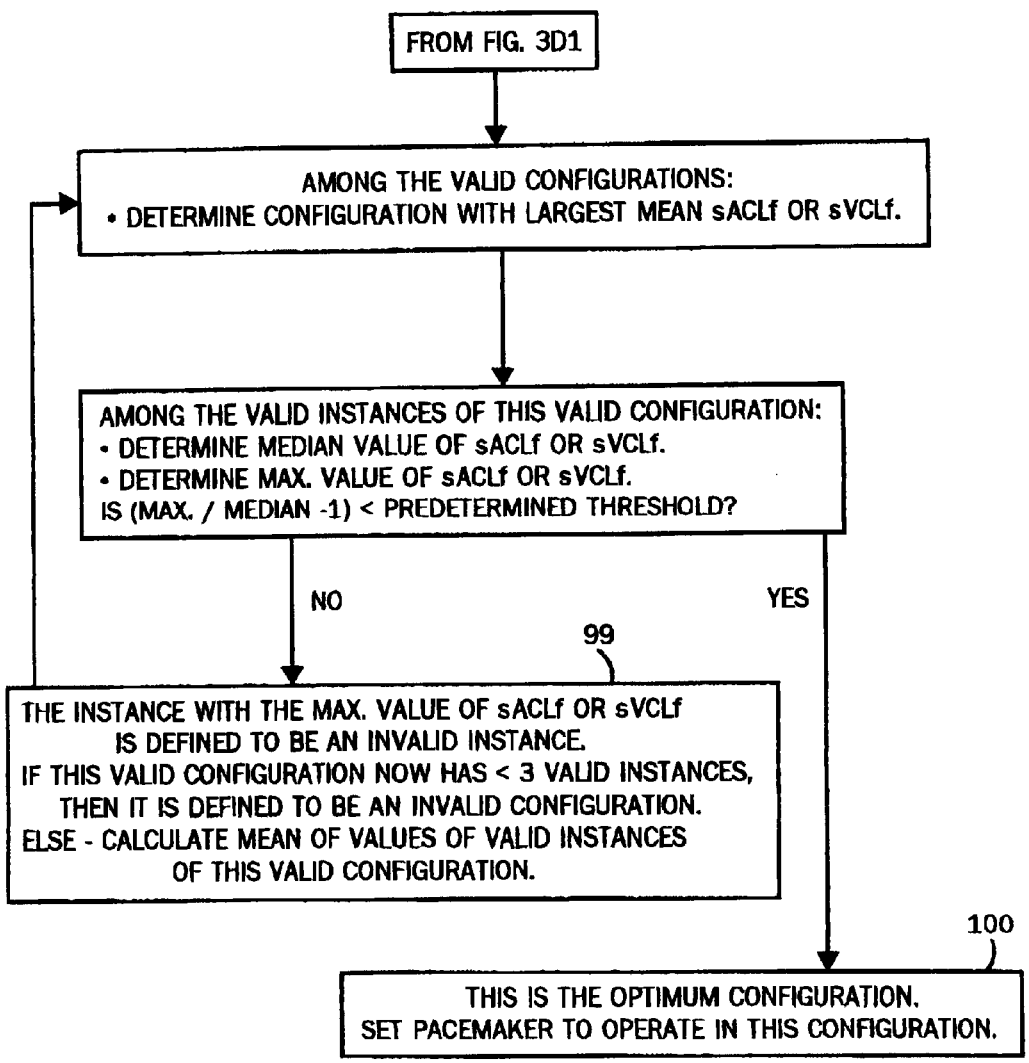
FIG. 3D2

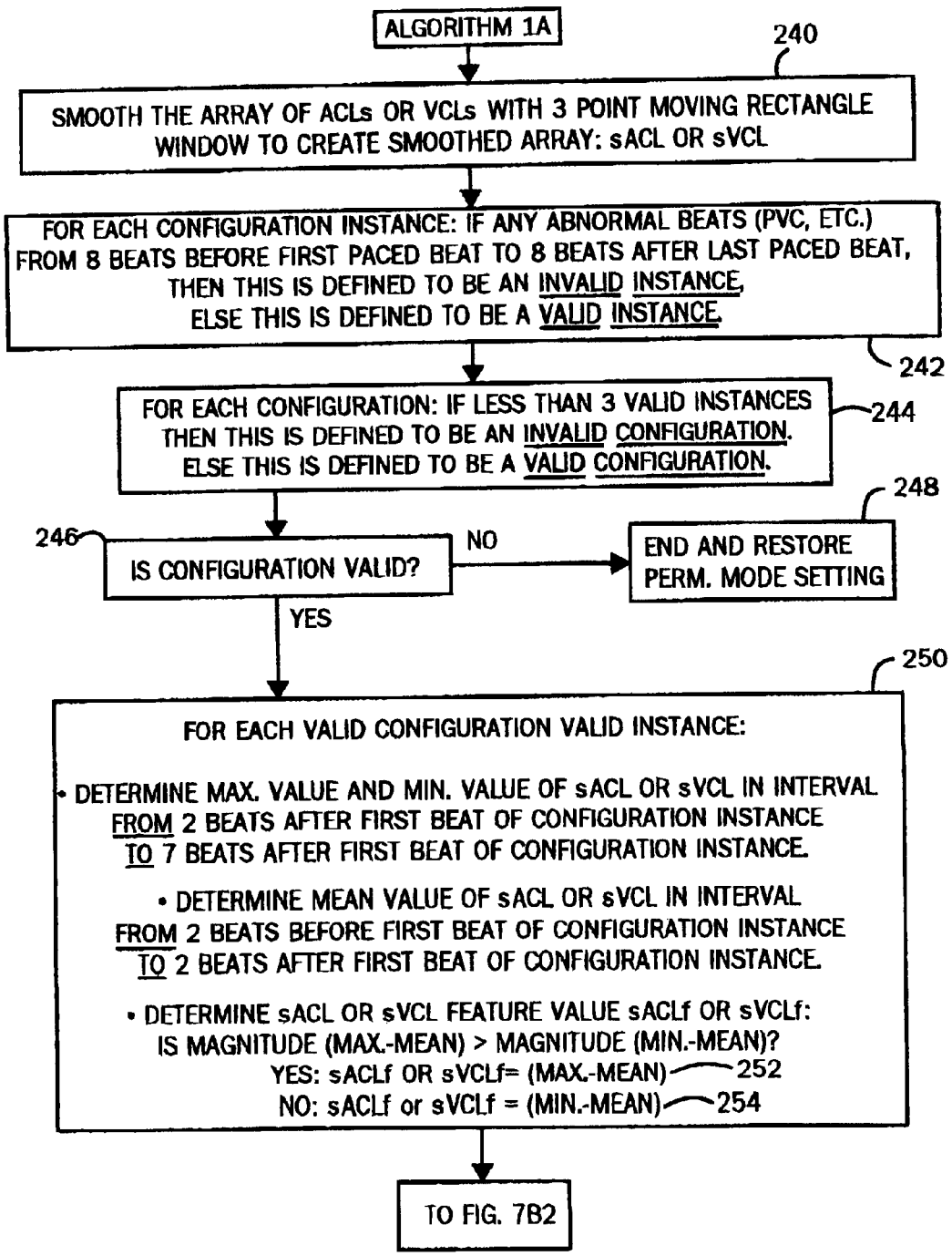
FIG. 7B1

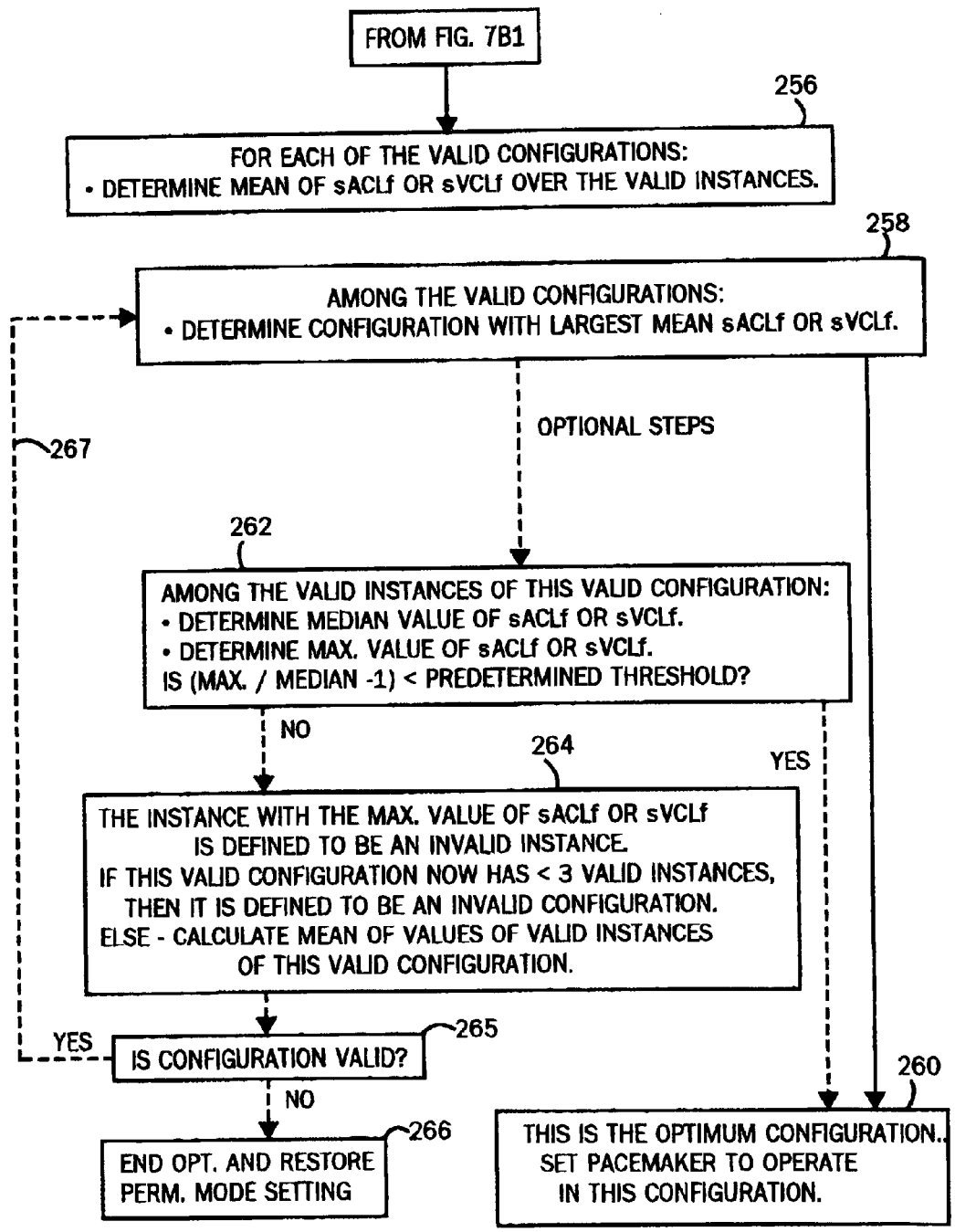
FIG. 7B2

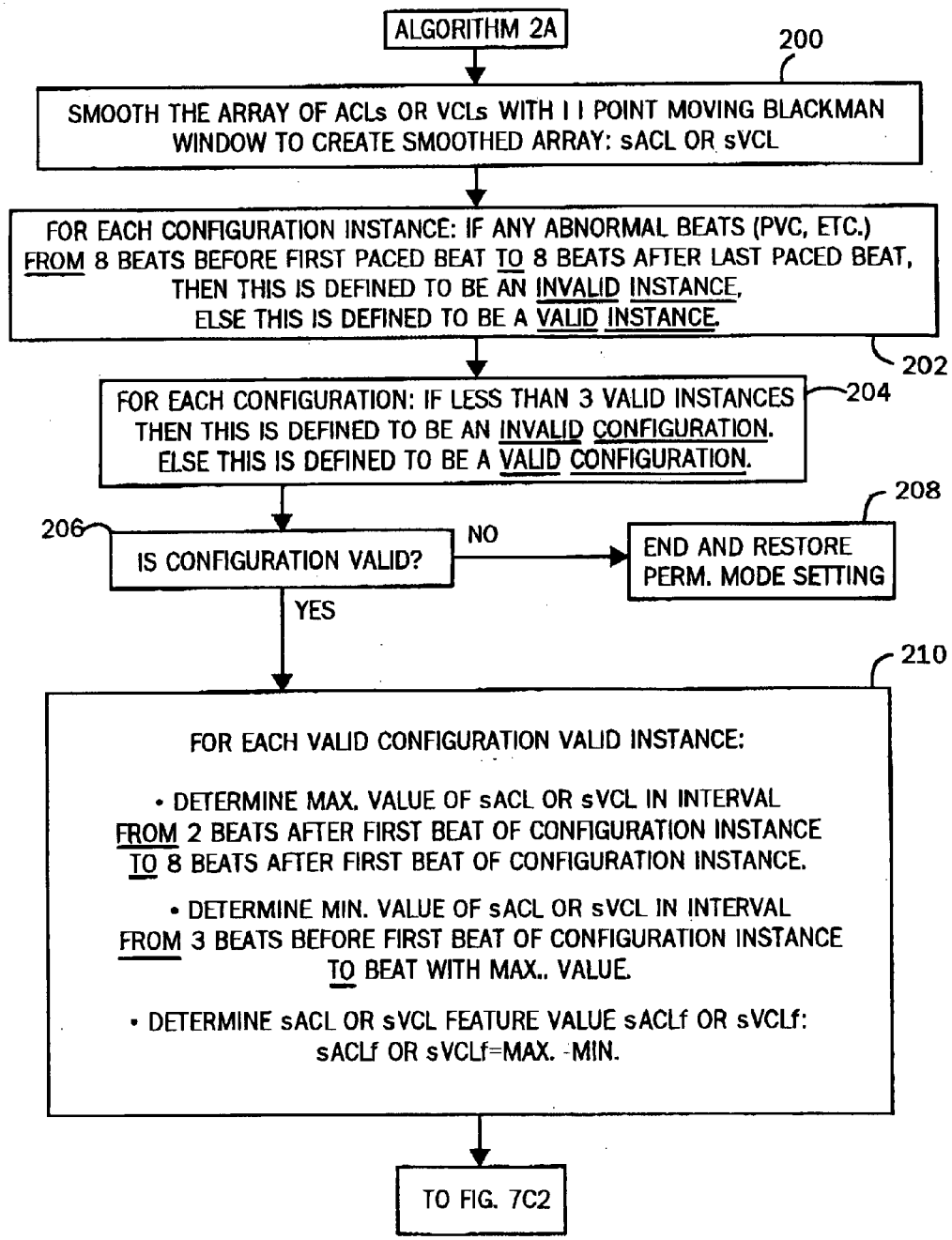
FIG. 7C1

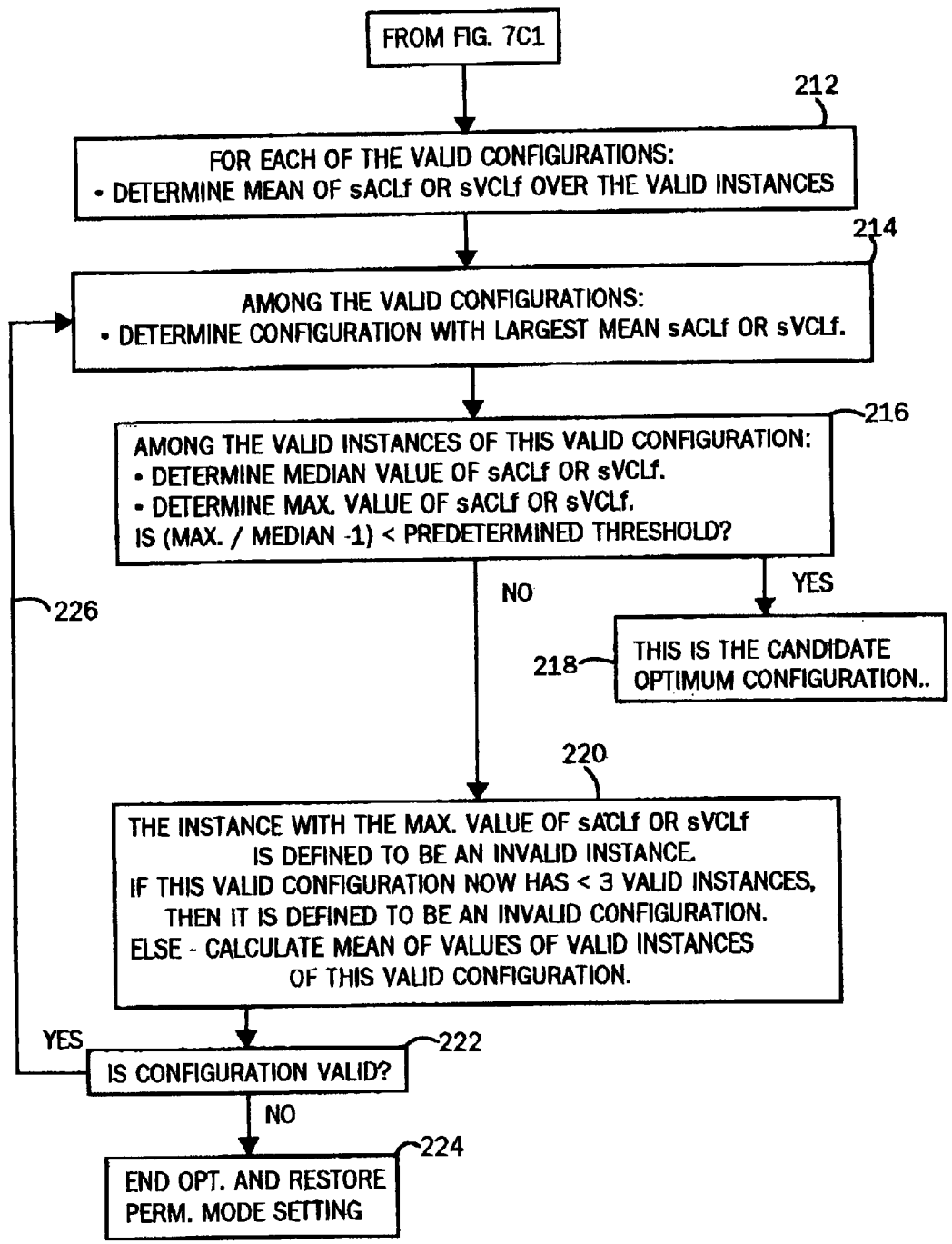
FIG. 7C2

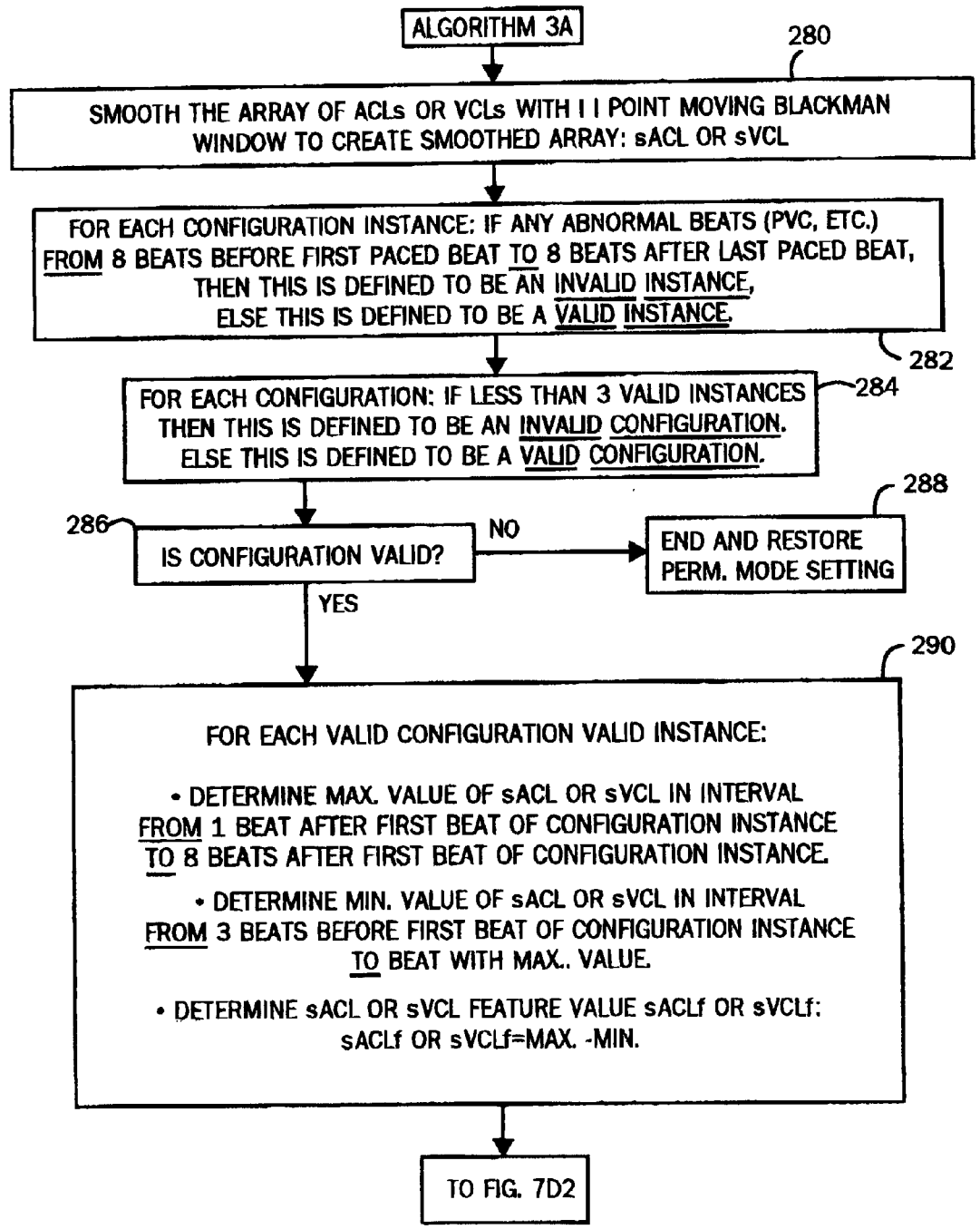
FIG. 7D1

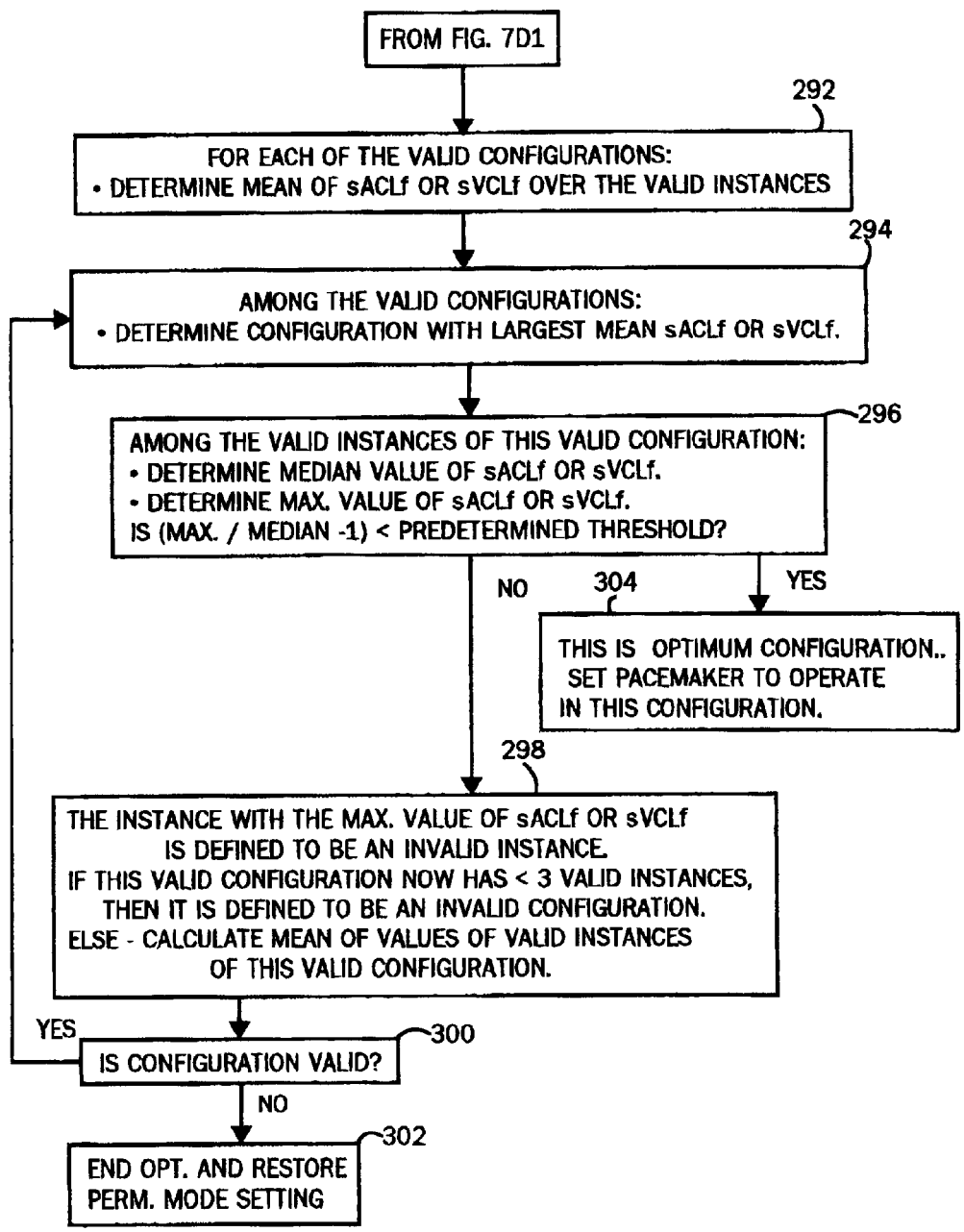
FIG. 7D2

CARDIAC RHYTHM MANAGEMENT SYSTEM WITH OPTIMIZATION OF CARDIAC PERFORMANCE USING HEART RATE

CROSS REFERENCE TO RELATED APPLICATION

This application is a continuation-in-part of application Ser. No. 09/545,536, filed Apr. 7, 2000. That application is deemed incorporated by reference in its entirety.

BACKGROUND OF THE INVENTION

1. Field of the Invention

This invention relates generally to implantable cardiac rhythm management devices, and more particularly to a method for establishing an optimum pacing mode and delay parameters for multiple pacing sites in a dual chamber implantable programmable pacemaker.

2. Related Art

An earlier patent to Baumann, a co-inventor herein, U.S. Pat. No. 4,800,471, assigned to the assignee of the present invention, the teachings of which are hereby incorporated by reference, explains that cardiac pacing can be used to improve hemodynamics in congestive heart failure (CHF) patients. One recognized and accepted indication of hemodynamic performance is reflected in the patient's pulse pressure (PP) which is defined as the difference between systolic aortic pressure and diastolic aortic pressure. PP could be used to optimize the pacing parameters in applying CHF therapy, however, this would require the use of a suitably positioned pressure sensor.

The Baumann '471 patent recognizes that an indirect indication of PP can be derived from the patient's atrial cycle length (ACL), which is the duration of the interval between consecutive P-waves in an ECG signal. The earlier Baumann patent discloses a method for using ACL to optimize CHF therapy parameters that involves looking at a transient sequence in which, after a period of intrinsic cardiac activity, a short predetermined sequence of pacing stimuli is delivered to the patient's heart. Any subsequent transient increase in measured ACL provides an indication of the therapy's effectiveness over intrinsic cardiac activity. Likewise, a subsequent transient decrease in measured ACL is indicative that the pacing therapy is non-beneficial.

In applying the methodology to an implantable, microprocessor-based controller of the type typically used in a programmable dual-chamber pacemaker, the device is made to cycle through transient paced beats with different pacing mode and AV delay configurations. Each such configuration is defined to be a group of consecutive beats with the same paced AV delay and the same pacing mode (right ventricular, left ventricular or bi-ventricular pacing). Each of the configurations is immediately preceded by a group of baseline beats. In the disclosed arrangement, three different pacing modes and five different AV delays are used, with each such delay being shorter than a previously measured value of the intrinsic AV delay. The particular mode/AV delay combination that results in the largest increase in ACL is then programmed into the pacemaker to thereby optimize hemodynamic performance of the patient's heart. To avoid inaccuracies due to noise, the algorithm described in the Baumann '471 patent is made to vary the order of therapy; randomization and averaging techniques are then used to extract data from repeated tests.

While the above approach has proved to be a useful tool, it does not take into account variations in time between pulse events with respect to pacing at multiple sites. It is common to stimulate both ventricle chambers, for example, and particularly the left ventricle can be provided with a plurality of sequentially paced sites. Each of these is operated using a timed delay sequence which may be selected from a menu of sequence timings which itself may change as data regarding patient history accumulates. Thus, if all paced sites could be integrated into an optimal pacing rhythm, additional benefit could be accorded the patient.

SUMMARY OF THE INVENTION

The foregoing features and advantages of the invention are achieved by providing an improved method for optimizing the inter-site delay and pacing mode configuration of an implanted, programmable pacemaker when treating CHF patients. The pacemaker involved is of the dual chamber type that includes an atrial sense circuit, a ventricular sense circuit and a pulse generator for applying cardiac stimulating pulses selectively to the right ventricular chamber, the left ventricular chamber or both chambers sequentially (bi-ventricular pacing). A plurality of pacing sites may be located in a single chamber, usually the left ventricle, and these are also paced using a time variable delay sequence.

The patient's intrinsic atrial depolarization events are tracked and from such events the ACL is measured over a first predetermined number of heartbeats, $N_1$, to establish a baseline value. At least one of the inter-site delay interval and the pacing mode configuration is changed for a predetermined number of stimulated heartbeats, $N_2$ and, again, the ACLs between successive paced beats is measured. These steps are repeated in iterative cycles until all of the preprogrammed inter-site delay intervals and ventricular chamber options have been utilized.

Subsequently, a comparison is made to determine which configuration of pacing mode and inter-site delay values resulted in the maximum increase ACL and those values are then programmed into the pacemaker. In that maximum increase of ACL correlates with maximum increase of PP, hemodynamic performances are thereby optimized. Additional performance parameters may also be used to correlate to PP or other relevant indicators of cardiac performance, these performance parameters include: ventricular volumes, blood flow velocity, total acoustic noise, and direct measurement of pressure.

As used herein, the terms "site-to-site delay" and "inter-site delay" mean the time interval between any sequential pacing events in the same cardiac cycle regardless of whether they occur in different or the same chamber. Thus, AV, V—V, $V_1$-$V_2$ (same chamber), A—A etc. may be represented depending on the pacing configuration.

The optimization determination is first made with the patient at rest to determine the most advantageous pacing mode. Thereafter, a one or more additional or periodic determinations can be implemented with the patient exercising or otherwise in an active state employing the technique to determine the optimum site-to-site delays and enable dynamic site-to-site delays to be implemented based on activity level. This empowers the system to implement dynamic site-to-site delays on its own based on an internal monitoring system.

BRIEF DESCRIPTION OF THE DRAWINGS

The foregoing features, objects and advantages of the present invention will become apparent to those skilled in the art from the following detailed description of a preferred embodiment, especially when considered in conjunction with the accompanying drawings in which.

DESCRIPTION OF THE PREFERRED EMBODIMENT

Figure 1:
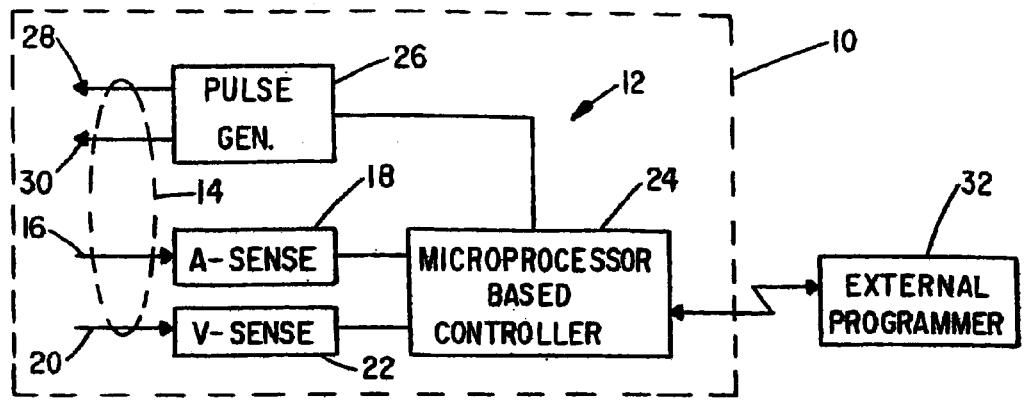
FIG. 1 is a schematic block diagram of a dual chamber pacemaker incorporating a microprocessor-based controller for pacing at a plurality of sites in which the inter-site delay parameters are optimized in accordance with the protocols and algorithms disclosed herein.

The present invention provides a method for establishing an optimum pacing mode and delay parameters for multiple pacing sites in a dual chamber implantable programmable pacemaker. The invention is described below in the context of utilizing atrial cycle length as the measured parameter for assessing the efficacy of the pacing mode and delay parameters. One skilled in the art will recognize that a variety of alternative performance parameters may be used to determine the efficacy of the pacing mode and pacing parameter. These performance parameters include ventricular volumes, blood flow velocity, total acoustic noise, and direct measurement of pressure.

These performance parameters may be assessed with a number of specific methods. That is, there are a many ways of assessing cardiac function including systolic function and/or diastolic function of a heart, that may be incorporated into an implantable microcontroller based cardiac pacemaker. Thus, for example, the cardiac function sensing circuit may measure intracardiac impedance variations due to the influx and outflow of blood from one of the ventricular chambers. This method is discussed in U.S. Pat. Nos. 4,686,987 and 4,674,518 to Salo, which are hereby incorporated by reference. Using this method it is possible to assess ventricular volume, stroke volume, cardiac ouput and derivatives of these parameters.

The cardiac function sense circuit may also comprise an accelerometer for measuring heart sounds or total acoustic noise (TAN). The TAN corresponding to optimal mechanical timing of the heart may be measured using an implantable accelerometer as disclosed in U.S. Pat. No. 6,044,298 to Salo et al, hereby incorporated by reference. It is also contemplated that a micromachined piezoelectric pressure transucer may be mounted on the right or left ventricular pacing lead where it may measure right or left ventricular pressure parameters such as end-diastolic or end systolic pressure or derivatives of these pressures corresponding to ventricular contractility.

The cardiac function sense circuit may also comprise a Doppler flow meter having a flow sensor operatively positioned relative to the aorta or pulmonary artery for measuring peak aortic or pulmonic flow velocity from which measures that are directly correlated to stroke volume and cardiac output may be derived. Similar measurements may be made of mitral or tricuspid flow velocity.

In one aspect, the present invention uses a stroke volume feature to predict the optimum pacing site which can be right ventricular (RVS), left ventricular (LV) or bi-ventricular (BiV), the optimum AV delay (Avdly), or a combination of both for an individual patient. As indicated, it consists of pacing protocols that execute a series of trials, each of which alternates between a baseline period (intrinsic condition) and a short pacing period at a given pacing site (PS)/AV delay combination. The transient change observed in the atrial cycle length (ACL) or ventricular cycle length (VCL) of the patient is collected for each trial, the data analyzed and the optimum PS and AV delay are selected based on the combination that produced the maximum increase in ACL or VCL over baseline.

Generally and exemplary of the invention, while not limiting, the optimization of AV delay may be selected and the system will thereafter perform according to one of several modes as will be described.

The following definition of terms apply to the ACL protocol and optimization analysis algorithms:

configuration—unique combination of pacing site (RV, LV or BiV) and AVdly (ms.).

washout period—A predetermined number, usually 10 consecutive cardiac cycles, where intrinsic AV conduction delay is detected and ACL measurements are collected normal baseline—A predetermined number, usually 5 consecutive cardiac cycles, where intrinsic AV conduction delay is detected and ACL measurements are collected pacing period—A predetermined number, usually 5 consecutive VDD paced cardiac cycles at a predetermined PS/AVdly combination, where ACL measurements are collected changed baseline—A predetermined number, usually 10 consecutive cardiac cycles after a pacing period, where intrinsic AV conduction delay is detected and ACL measurements are collected instance or trial—one sequence of normal baseline+pacing period+changed baseline at a particular PS/AVdly.

Referring now to FIG. 1 representing a preferred embodiment, there is shown enclosed by a dashed-line box 10, a cardiac rhythm management device, here depicted as a VDD bradycardia pacemaker 12, which is adapted to be operatively coupled to a patient's heart by means of a conventional pacing lead 14. In particular, an atrial sensing electrode disposed in the right atrium of the heart is coupled by a wire 16 in the lead 14 to an atrial sense amplifier 18. Similarly, a ventricular sensing electrode disposed in the right ventricle is connected by a wire 20 in the lead 14 to a ventricular sense amplifier 22 contained within the pacemaker 12. Thus, when the SA node in the right atrium depolarizes, the resulting signal is picked up by the atrial sense amplifier 18 and applied to a microprocessor-based controller 24 which will be more particularly described with the aid of FIG. 2. Ventricular depolarization signals (R-waves) are likewise amplified by the ventricular sense amplifier 22 and applied as an input to the microprocessor-based controller 24.

The microprocessor-based controller 24 is connected in controlling relationship to a pulse generator 26 to cause a ventricular stimulating pulse to be applied, via conductor 28 in lead 14, to tissue located proximate the apex of the right ventricle (RV) to initiate ventricular depolarization that spreads as a wave across both the right and left ventricles. The pulse generator 26, under control of the microprocessor-based controller 24, can also be made to apply stimulating pulses over a wire 30 in lead 14 to stimulate the heart's left ventricle (LV). If the pacing mode calls for biventricular pacing, the pulse generator 26 is controlled by the microprocessor-based controller 24 to deliver stimulating pulses to sites in both the right and left ventricles (BV). In accordance with contemporary techniques, the left ventricle additionally may be sequentially paced at a plurality of locations (sites).

The microprocessor-based controller 30 controls the timing of stimulating pulses at cardiac sites relative to a selected preceding depolarization signal and to each other to thereby define site-to-site pulsing intervals. The system is capable of pacing in several modes and at variable site-to-site time delays in each mode.

An external programmer 32 is arranged to send data signals transcutaneously to the implanted pacemaker 12 and also to receive signals originating within the pacemaker. In this fashion, a physician is capable of programming such parameters as pacing rate, pacing pulse width, pacing pulse amplitude, sensitivity, AV delay interval, etc., in a fashion known in the art. The external programmer may also be used to receive signals and pass them on to an external monitor (not shown) incorporating a microprocessor and associated memory.

Figure 2:
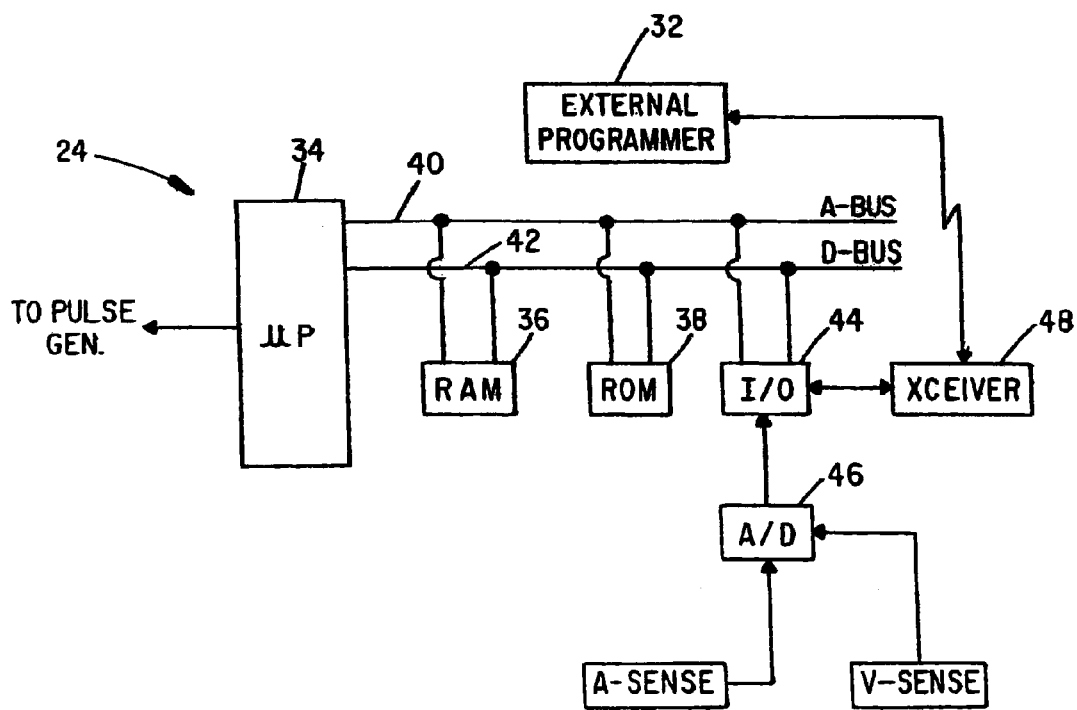
FIG. 2 is a schematic block diagram of the microprocessor-based controller incorporated into the pacemaker of FIG. 1.

FIG. 2 shows a more detailed block diagram of the microprocessor-based controller 24 shown in FIG. 1. It is conventional in its architecture and includes a microprocessor chip 34 and associated RAM and ROM memory modules 36 and 38 connected to it by an address bus 40 and a data bus 42. As is known in the art, the RAM memory 36 is a read/write memory comprising a plurality of addressable storage locations where multi-byte data words and operands used in the execution of one or more programs may be stored for subsequent readout. The ROM memory 38 will typically be used to store the control programs executable by the microprocessor chip 34.

Also connected to the address bus and data bus is an I/O interface module 44. If a separate analog-to-digital converter, as at 46, is utilized rather than an on-board A/D converter forming a part of the microprocessor chip 34, its output will be connected through the I/O module 44 allowing the analog outputs from the atrial sense amplifier 18 and the ventricular sense amplifier 22 to be digitized before being routed to the microprocessor chip 34. If the particular microprocessor employed incorporates an on-board A/D converter (as is somewhat conventional), then the outputs from the A-sense amplifier 18 and V-sense amplifier 22 are applied directly to appropriate inputs of the microprocessor chip 34.

Also coupled to the I/O module 44 is a transceiver 48 that is used to interface the external programmer 32 to the implanted pacer 12. The manner in which an external programmer appropriately placed on the chest wall in proximity to the implanted device is capable of transmitting digitally encoded data therebetween is well known to those skilled in the pacemaker art.

Figure 3:
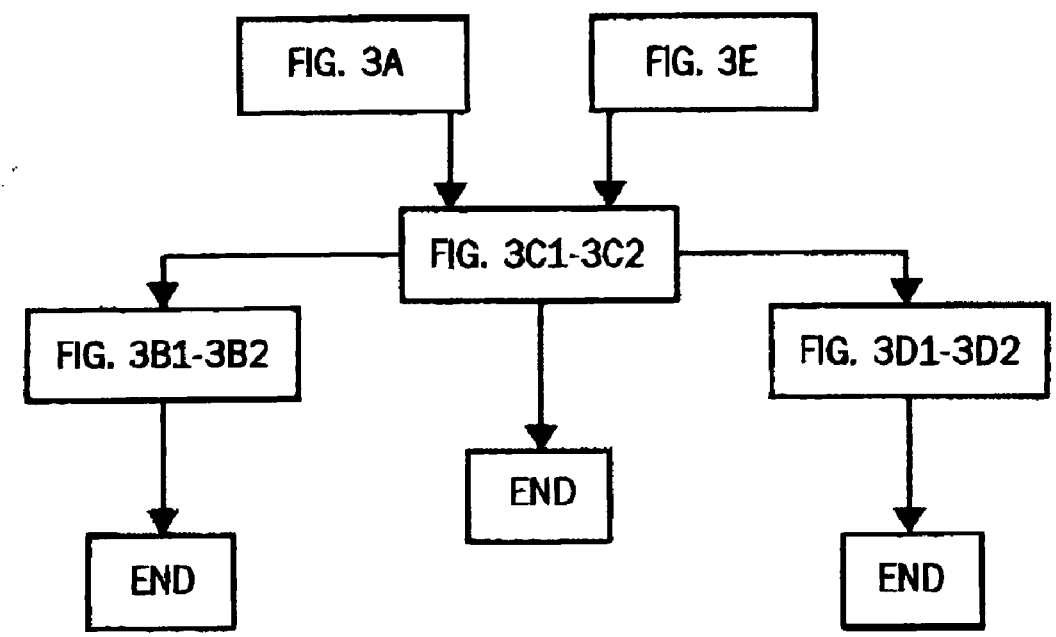
FIGS. 3A, 3B, 3C, 3D and 3E, when arranged as shown in FIG. 3, illustrate a flow diagram for one optimization protocol including algorithms of the present invention.

FIGS. 3A, 3B, 3C, 3D and 3E when arranged as shown in FIG. 3 comprise a flow chart of the algorithms executed by the microprocessor 34 in arriving at an optimal pacing mode and inter-site delay combination for a patient in which the system of the present invention is implanted.

Before explaining the steps of the algorithm in detail, a brief overview of the methodology is deemed helpful.

The algorithms can be executed by the microprocessor-based controller in the pacer or in an external microprocessor in the monitor/programmer 32. In the following description, it is assumed that the control algorithms are executed by the microprocessor 34 in the implanted device. The algorithms, using cardiac atrial cycle lengths measured in the VDD pacemaker, determines a patient's optimum pacing mode and inter-site delay configuration, which is the mode (e.g., RV, LV, BV, RV and $LV_1$, $LV_2$, etc.) and inter-site delay during VDD pacing which maximizes cardiac function (e.g., PP) for the patient. The pulse generator 26 is then set to operate at this optimum pacing mode and inter-site delay.

The optimal pacing mode and associated optimum inter-site delays are determined from the maximum (or minimum) value of one of several empirically derived features which are calculated from the atrial cycle lengths. In particular, the atrial cycle lengths immediately following a transition from an intrinsic or paced baseline (BL) to a paced mode, inter-site delay, i.e., during a transient period of the paced mode and inter-site delay, is used. Thus, this invention eliminates the need for a period of waiting for hemodynamic stability to be reached during the paced mode and particular inter-site delay.

The pulse generator will be made to cycle through a predetermined number of intrinsic or paced BL beats followed immediately by paced beats using a first mode and inter-site delay configuration, followed immediately by additional intrinsic or paced BL beats, followed immediately by beats of a second mode and inter-site delay configuration, etc., until all of the possible programmed configurations have been utilized. The ACL between successive beats is computed and stored as an array in the RAM memory of the microprocessor-based controller.

Once the array of ACL values are stored, they are subsequently processed to arrive at values of ACL features. In particular, the array of values may be smoothed using a 3-point moving rectangle window or an 11-point moving Blackman window. Then for each configuration and repeated instances thereof, further computations are made to identify the particular configuration exhibiting the largest average of the smoothed ACL features. It is this configuration that is determined to be the optimum and the pacemaker is then set to operate in this optimum configuration. The automatic selection of optimal mode delay which is found to optimize cardiac function eliminates any need for manual programming of the implanted pacemaker by the physician.

The algorithms of the present invention are based upon a hypothesis that if a transient change in atrial cycle length is large positive, then the transient change in aortic pulse pressure is also large positive. Thus, the largest positive change in atrial cycle length predicts the largest positive change in aortic pulse pressure.

There is a physiological basis for this relationship. A large, sudden increase in the aortic pressure (in this case due to the sudden change from baseline cardiac function to paced mode inter-site delay cardiac function) is sensed by arterial barroreceptors, and the reflex mechanism of the Autonomic Nervous System (ANS) tries to drive the aortic pressure back to its previous stable (in this case, baseline) value by increasing the atrial cycle length. The ANS acts as a negative feedback control system for the aortic pressure.

The paced mode and inter-site delay associated with the largest mean increase in ACL is hypothesized to be the optimum paced mode and inter-site delay for the pacemaker. The optimum is the one that provides a maximum increase in aortic pressure over baseline aortic pressure for the then-current state of activity of the patient. As will also be seen, this may change with increased levels of activity in the patient.

With the foregoing summary in mind, then, attention is directed to the flow charts of FIGS. 3A through 3D. The first step in the algorithm is to derive a baseline. The pulse generator is initially inhibited while intrinsic cardiac activity is sensed such that a value of the patient's intrinsic AV delay and ACL can be measured. Next, the physician may generate a list of all possible combinations of three pacing modes and a predetermined number of inter-site delay values where each of the delay values is set as desired. While a different number of paced inter-site delay values can be selected, arbitrarily and for purposes of explanation of the inventive algorithm, it will be assumed that five different inter-site values are established by the physician. These may include a plurality of pacing sites in the same chamber and/or sites in several chambers. Generally, plural sites will be limited to the left ventricle, however. This leads to 3×5=15 possible configurations as indicated in block 52.

Figure 3A:
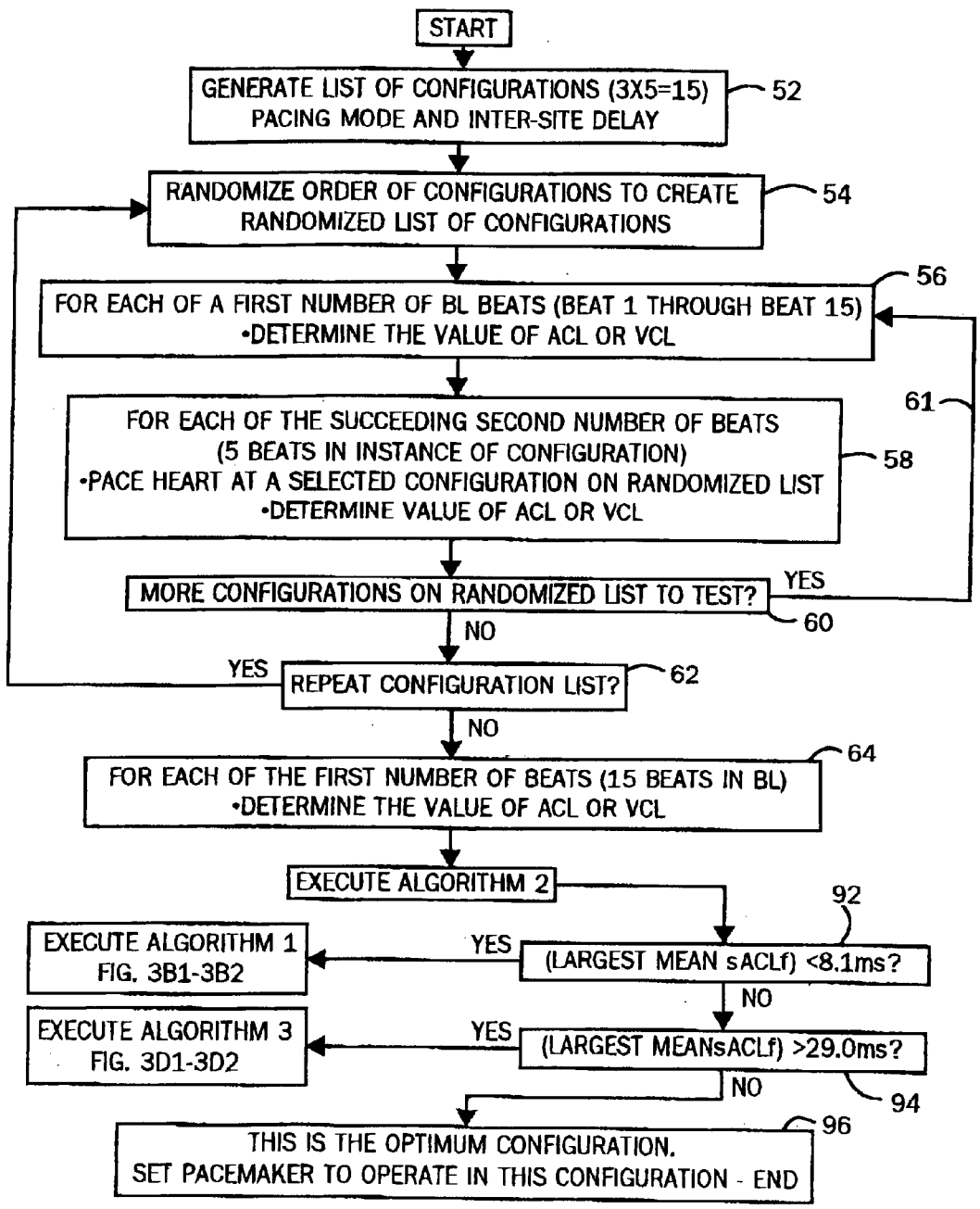

To avoid any influence that the particular order in which the configurations are employed in pacing the patient, the list generated in step 52 is randomized as reflected in block 54 in FIG. 3A.

Again, without limitation, a string of beats with the pulse generator inhibited may be used to establish BL and then for each of these baseline beats, the atrial cycle length between them is determined. As earlier mentioned, rather than using intrinsic inter-site delays to establish BL, the BL can also be at a particular configuration of pacing mode and inter-site delays. In the description to follow, a group of at least 15 sequential beats are generated. The ACL measurement may be performed in the microprocessor by initiating a timer upon the occurrence of a P-wave in the cardiac electrogram and stopping the timer upon detection of the next succeeding P-wave. The ACL value associated with each BL beat is then stored as an array in the RAM memory 36.

Referring again to the block diagram of FIG. 3A, immediately following the last of the beats used in establishing BL, the heart is paced using a selected configuration drawn from the randomized list developed at block 54. Again, without limitation, the second number of beats may equal five. As with the BL beats, the ACL for the paced beats is also determined as reflected in block 58.

A test is next made at block 60 to determine whether all of the 15 possible configurations on the randomized list have been used and the ACL values associated therewith stored in the memory.

If not all of the configuration possibilities have been exhausted, control returns over path 61 to block 56 and the operations reflected in blocks 56 and 58 are repeated until all of the possibilities have been exhausted. So that any anomalies which may have occurred in the measurement of the respective ACL values can be averaged out, steps 54, 56, 58 and 60 are repeated a predetermined number of times, e.g., five times, to obtain additional instances of the configurations that can later be averaged. See decision block 62.

The change in PP caused by the five paced beats in step 58 is immediate. There is no time delay. However, the change in ACL caused by the reflex mechanism of the Autonomic Nervous System in response to this change in PP is not immediate. There is a time delay of several beats. Thus, the delayed change in ACL can occur during the 15 BL beats in step 56 which follow the five paced beats in step 58. Thus, the final 15 or more BL beats in step 64 are needed to follow the final five paced beats in step 58.

Once the raw ACL values have been computed and stored as an array in the RAM memory, further algorithms may be used to process the raw data in arriving at the particular pacing mode-AV delay configuration yielding optimum hemodynamic performance.

Algorithm 2 shown on FIG. 3C is executed to first select candidates for being the optimum configuration of pacing mode and inter-site delays. Here at block 77, the raw ACL data (or VCL data) are first smoothed using a known signal processing approach referred to as an 11 point moving Blackman window which yields a smoothed ACL array, (sACL). At block 78, a determination is made as to whether any abnormal beats, e.g., PVCs, occurred during an interval from eight beats before the first transient pace beat to 8 beats after the last transient paced beat. If abnormal beats are detected, the collected data is defined to be an "invalid instance". If no such abnormal beats occurred, it is defined to be a "valid instance". Next, and as reflected by block 79, for each configuration, a determination is made as to whether less than three "valid instances" occurred and, if so, it is defined to be an "invalid configuration". On the other hand, if three or more valid instances occur, it is defined to be a "valid configuration".

Figure 5:
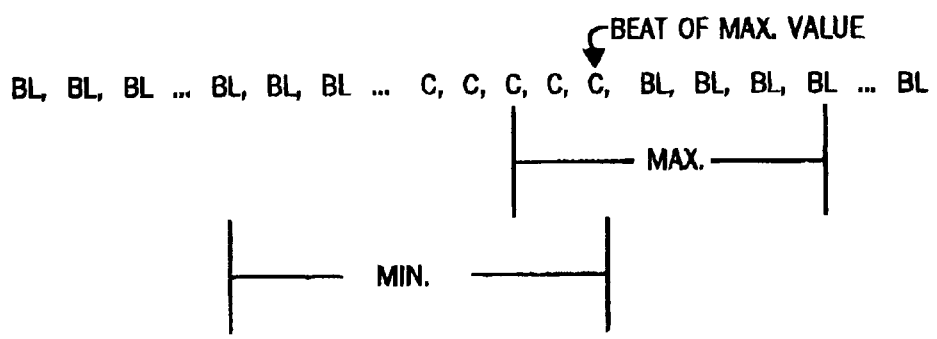
FIG. 5 is a drawing similar to FIG. 4 for a second algorithm.

Next, as indicated by block 80, for each valid instance of a valid configuration, a determination is made as to the maximum value of sACL values in an interval from two beats after the first beat of a configuration instance to eight beats after the first beat of the configuration instance. Likewise, a minimum value of sACL values in an interval from three beats before the first beat of the configuration instance to the beat with the maximum value is determined. FIG. 5 is helpful in defining the respective intervals in which the maximum values and minimum values are to be found. Once the maximum value and minimum value in the respective intervals have been determined, a smoothed ACL feature value, referred to in the flow charts by the acronym sACLf, is computed as the maximum value minus the minimum value.

Upon completion of step 80, for each of the valid configurations of mode and inter-site delays, the mean of the sACLf values over the number of valid instances of a given configuration is computed. See block 82. Next, out of the previously determined valid configurations, the configuration exhibiting the largest mean sACLf is computed (block 84).

Once the particular configuration exhibiting the largest mean sACLf is determined, via step 84, the number of valid instances where the particular valid configuration has been repeated are examined to determine a median value and a maximum value of the smoothed ACL feature, sACLf. With the median and maximum values so determined, a test is made to determine whether the quantity (MAX/MEDIAN−1) is less than a predefined threshold. The purpose of this threshold test is to remove a MAX whose value is too large (relative to the median value). The "predefined threshold" has been determined empirically from data accumulated from a significant number of patients as a value of 9.5, which gave good results for the set of patients investigated.

If the result of the test is true, a potential candidate for the optimum configuration has been found (block 88). However, if the test at block 86 had proved false, the instance with the maximum value of sACLf is defined to be an invalid instance. If this valid configuration now has less than three valid instances, then it is defined to be an invalid configuration. If the valid configuration has three or more valid instances, the mean of values of valid instances are calculated for the valid configuration. Control then loops back over line 91 to block 84 to again repeat steps 84 and 86 until such time as the test set out in block 86 comes out "true".

Referring again to the flow diagram of FIG. 3A, after all candidates for the optimum configuration have been determined, further processing takes place to determine which of the candidates is the optimum configuration so that the pacemaker can be programmed to operate in this configuration. Specifically, a test is made at block 92 to determine whether the largest mean sACLf computed at block 82 is less than 8.1 milliseconds. If it is, algorithm 1 of FIG. 3B is executed. If not, a further test is made to determine whether the largest mean sACLf value is greater than 29.0 milliseconds. If so, algorithm 3 illustrated at FIG. 3D is executed. If the largest mean sACLf feature value lies between 8.1 milliseconds and 29.0 milliseconds, it is the optimum configuration and, as indicated by block 96, the pacemaker is programmed to operate with that configuration of pacing mode and AV delay. The 8.1 ms and 29.0 ms values have been empirically established by study of data obtained from a set of ten patients in a study.

Referring next to FIG. 3B, the details of Algorithm 1 will be further explained. The first step in Algorithm 1 is identified by block 66 and involves smoothing the array of ACLs with a 3-point moving rectangle window. The resulting sACLf values are then also stored in the RAM memory. While other smoothing techniques are known to persons skilled in signal processing, a 3-point moving rectangle moving technique proves to be simple to execute and produces reliable results.

As was the case with algorithm 2, tests are made to determine whether any abnormal beats occurred in the interval from 8 beats before a first paced transient beat to 8 beats after the last paced transient beat for each of the configuration instances and if such an abnormal beat did occur, that configuration instance would be determined to be invalid. Then, each configuration is examined to determine if three or more valid instances were found in that configuration and, if so, it would be defined to be valid. However, if a configuration was found to include less than three valid instances, it would be defined as an invalid configuration.

Figure 4:
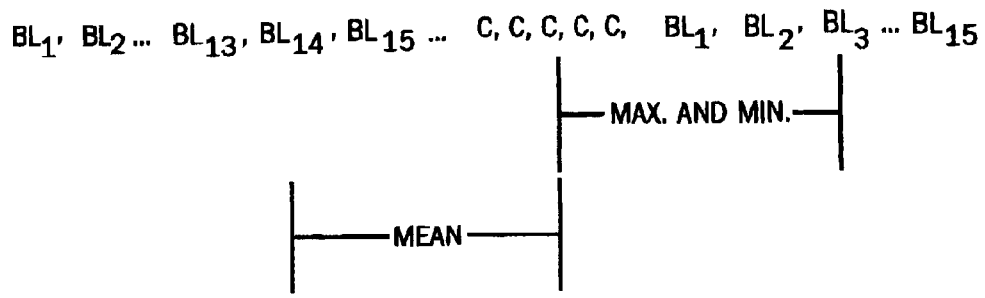
FIG. 4 is a representation of a series of baseline and paced beats useful in explaining the development of ACL features in accordance with a first algorithm.

Next, and as is reflected by block 67 in the flow diagram of FIG. 3B, for each valid instance of each valid configuration, the maximum value and the minimum value of the smooth ACL in an interval from two beats after the first beat of the configuration instance to seven beats after the first beat of the configuration instance are computed. This operation is further explained with the aid of FIG. 4. In FIG. 4, there is shown a series of 15 baseline beats, followed by five paced beats of an instance of a first configuration identified as C, again followed by another series of 15 baseline beats. The interval in which the maximum and minimum values of smoothed ACLs are to be located is labeled "MAX and MIN". Likewise, the interval in the which the mean value of the smoothed ACLs is to be located is identified by "MEAN". By selecting the intervals in the manner indicated, changes in ACL of a transient nature as distinguished from steady state is guaranteed. Once the MAX and MIN values of sACL for the configuration instance are known, a test is made to determine whether the absolute value of the quantity (MAX−MEAN) is greater than the absolute value of the quantity (MIN−MEAN) for the configuration instance. If the outcome of the test is true, then the smoothed ACL feature (sACLf) for the configuration instance is determined to be the quantity (MAX−MEAN). If the test is false, then sACLf is made to be (MIN−MEAN). See steps 68 and 69 in block 67.

Next, as is indicated by operation block 70, for each of the valid configurations, a computation is made to determine the average or mean of the sACLf over the number of valid instances of that configuration. Once the operation indicated by block 70 has been completed, the particular valid configuration exhibiting the greatest mean of smoothed ACL features is identified at block 71 and the pacemaker is automatically programmed to operate with this optimum configuration as shown in block 72.

An optional sequence of steps is shown connected to the flow chart by dashed lines. According to the optional steps, an outliers test may be performed at block 73 similar to that of algorithm 2 in FIG. 3C previously described to remove a MAX whose value is too large (relative to the median values). Again, the empirically determined (predetermined threshold) of 9.5 may be used. If the result of this test is true, as shown at block 72, this is the optimum configuration that has been determined and the pacemaker can be set to operate at that configuration. However, if the test at block 73 proves false, the instance with the maximum value of sACLf or sVCLf is defined to be an invalid instance and is shown in block 74. If this once valid configuration now has less than three valid instances or trials, then it is re-defined to be an invalid configuration. If the configuration still has three or more valid instances, it remains valid. Control loops back over line 75 to block 71 to again repeat steps 71 and 73.

Referring again to FIG. 3A, if the test at block 94 had established that the largest mean sACLf had been greater than 29.0 milliseconds, algorithm 3 shown in FIG. 3D would have been executed rather than algorithm 1. Referring to FIG. 3D, the steps therein are substantially identical to those of algorithm 2 shown in FIG. 3C with the first 3 blocks being the same as 77, 78 and 79; the 3 blocks of 98 being the same as 82, 84 and 86 of FIG. 3C and 99 being the same as 90. However, in block 97 of FIG. 3D (corresponding to block 80 in FIG. 3C), the maximum value of sACL (or sVCL) is determined at an interval of from one beat after the first beat of a configuration instance rather than from two beats after a first beat configuration instance. Secondly, block 100 in algorithm 3 shown in FIG. 3D differs from block 88 of algorithm 2 shown in FIG. 3C in that rather than identifying a candidate optimum configuration, the actual optimum configuration is established and the pacemaker is then programmed to operate in this optimum configuration.

Figure 3E:
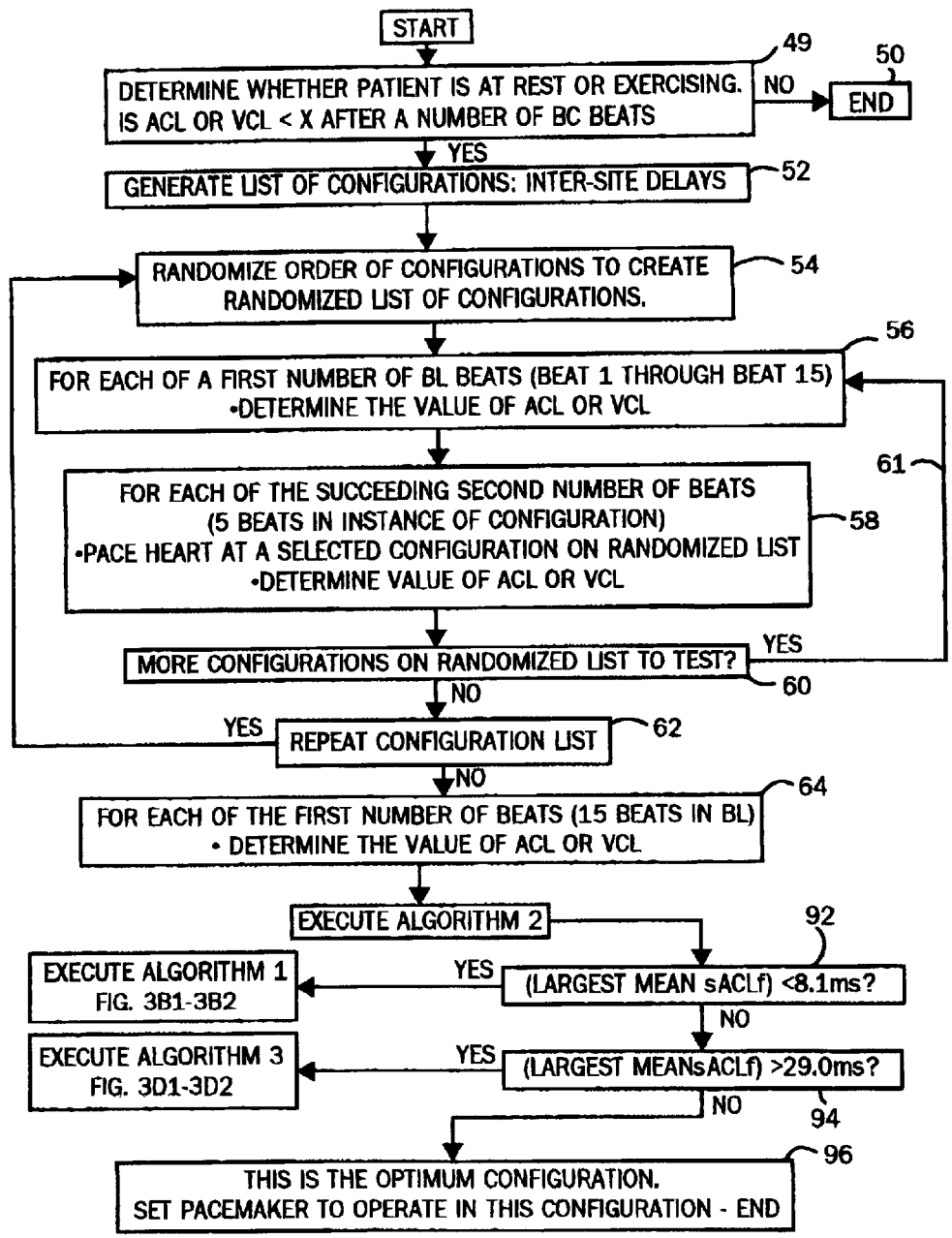

The above optimization is designed to be accomplished when the patient is asleep or otherwise in a sedentary state. The optimization algorithm, however, is also useful in optimizing pacing of the same individual during physical activities. This is illustrated in the flow diagram of FIG. 3E which differs from FIG. 3A only slightly. First, a determination is made at 49 based on intrinsic ACL or VCL (indicative of HR) as to whether the patient is exercising or at rest after a number of intrinsic beats are sensed. If the rate exceeds a predetermined limit, it is presumed that the patient is exercising. If it is determined that the patient is exercising, the algorithm of FIG. 3E is completed: otherwise the program ends at 50. The only difference in the determination in this situation is that the optimum pacing mode determined when the patient was at rest is retained and only the inter-site time delays are cycled and adjusted based on activity state. The result obtained yields an optimum dynamic value of the inter-site delays.

In accordance with the invention, a further specific alternate protocol embodiment for the determination of the optimum pacing sites (PS) and AV delay chosen also based on the combination that produces the maximum increase in the ACL over baseline will next be discussed. Of course, while generally described with regard to ACL, this example can also be applied to VCL if desired.

Figure 7:
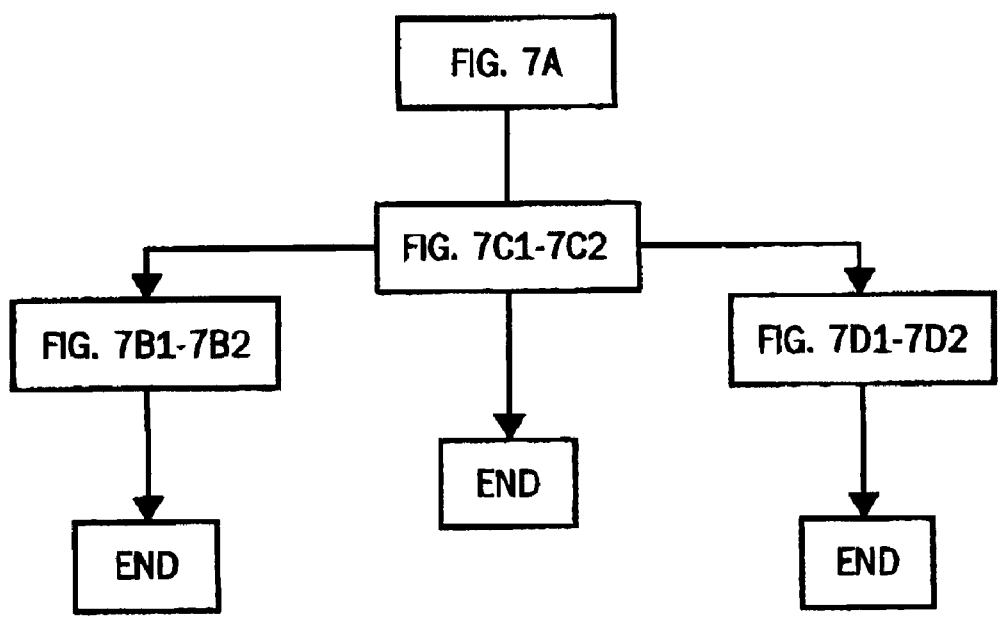
FIG. 7 illustrates the relationship of associated FIGS. 7A–7D which, in turn, illustrate flow charts of an alternative optimization protocol and associated algorithms.

Flow charts disclosing an alternate optimization protocol embodiment is shown in FIGS. 7A–7D associated in accordance with FIG. 7. The basic ACL (VCL) protocol is depicted in the flow diagram of FIG. 7A and is generally similar to that of FIG. 3A, but it includes several modifications, as will become apparent.

As with the protocol of FIG. 3A, the first step is to sense intrinsic cardiac activity such that a value of the patient's intrinsic AV delay and ACL can be measured. The measured intrinsic AV delay is later used as a basis for AV delay settings for optimization trials in the protocol of FIG. 7A.

To allow the system to measure intrinsic AV delay while providing ventricular backup pacing, the system sets the pacing device to operate in a VDD mode with a specific AV delay, perhaps 400 msec. LRL equal 240 ppm. After the transition of the device to this mode, the system waits for a washout period of 10 cardiac cycles before collecting intrinsic AV delay measurements shown at block 150 in FIG. 7A. To calculate the patient's intrinsic AV delay, the system averages a number, normally 10, intrinsic AV delay measurements after the waiting period. The AV delay masurements may be non-consecutive. Intrinsic AV delay is measured from the detection of an atrial sense outside of PVARP to the first succeeding ventricular sense in either ventricular chamber (LV or RV).

The protocol includes a time limit for the system to determine the patient's intrinsic AV delay and if it cannot be accomplished within this time limit which, in one embodiment, is 1 minute +/−2 seconds as shown at 152, the on-going attempt to initiate the optimization protocol is ended and the device is restored to its earlier permanent mode settings at 154. Once the intrinsic AV delay of the patient is successfully calculated within the allotted time, the system generates a list of configurations or trials which include a plurality of pacing sites and AV delays. Typically, 25%, 50% and 75% of the measured intrinsic Avdly value may be used (block 156). In that regard, a CHF flexstim protocol has shown that 25%–75% of PR range is one in which all responder patients exhibit maximum pulse pressure response to pacing.

Figure 8:
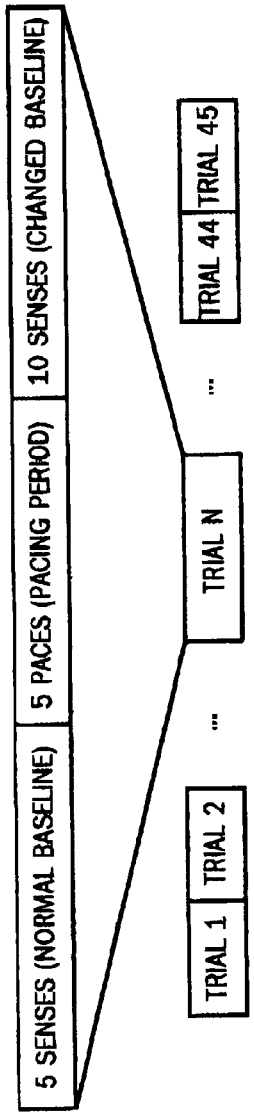
FIG. 8 illustrates schematically in block form the alternative protocol of FIGS. 7A–7D.

The system generates a randomized list of the unique PS/AV delay combinations at 158 to be repeated a number of times, generally 5, with each repeat of the list being in a re-randomized order. For example, if 3 PS and 3 AV delay optimizations are selected and the trials are repeated a total of 5 times, the ACL protocol will consist of 45 trials. This example is further illustrated in the schematic representation of FIG. 8.

A string of beats is used to establish baseline (BL) for each trail or instance using a particular configuration of pacing mode and inter-site delay as shown at 160. Again, with reference to FIG. 8, this is normally 5 beats and the ACL measurement is performed in the microprocessor and stored in the RAM memory 36 as previously described in relation to the previous embodiment. Immediately following the last of the beats used in establishing BL, the heart is paced using a selected configuration drawn from the randomized list developed in Block 158 again, without limitation, the second number of beats may equal 5. As with the BL beats, the ACL for the paced beats is also determined as reflected in block 162. Thereafter, is shown at 164 the changed baseline for the trial is initiated and the measurements are made for the succeeding 10 beats. Each instance or trial then consumes 20 beats.

Thereafter, a determination is made whether the trial is invalid at 166 and if the trial just completed is found to be invalid due to an abnormal beat or other anomaly, many of which are enumerated below, a washout period is initialized at 168 and a determination is made at 170 whether the washout was accomplished (noting 10 consecutive normal beats) within a predetermined time such as one minute +/−2 seconds at 170. If time has expired for the washout to be completed. The optimization protocol is ended and the permanent mode settings are restored at 171. An inquiry is then made at 172 as to whether this trial is a repeat of the previous trial and, if not, at 174 the particular trial is immediately repeated once via 160. A once repeated trial which again results in an invalid trial remains noted as an invalid trial and the system moves on to the next trial at 176 as signalled on line 177.

Reasons for invalidating a trial include, but may not be limited to, the following:

1. The device cannot pace the ventricle(s) during the pacing period at the programmed AV delay except for the first ventricular pace after transitioning from the normal baseline to the pacing period;

2. The ventricular sense is not detected during baseline;

3. If any abnormal beats, e.g., PVCs, are detected anywhere in the trial; and

4. Noise is detected in a trial or ventricle channels during the pacing period (inhibit or pace programmed).

With respect to the washout periods utilized, washouts can also be invalidated under a number of conditions as follows:

1. Ventricular sense not detected; and

2. An abnormal beat, for example, PVC or PAC as detected.

As shown at 178, via 179, trials continue until the list of configurations has been exhausted as when TN equals 9. Thereafter, the instance or list repeat number, N, is incremented at 180 and, at 182, the total number of cardiac cycles (cc) that have been used during the test is checked against a predetermined total number necessary for the completion of the basic ACL protocol which, in this case, is 10 cc+(20 cc/trial×9 trials or instances×5 (max N)=910 cc). A factor such as 20% additional cc is allowed for repeats and washouts. If this has not been exceeded, the trials continue at 184 via line 185. When N exceeds N Max or reaches 6 after being incremeted at 180, the initial or data gathering phase of the optimization is finished. The raw ACL values have been computed and stored in an array in the RAM memory and, as in the previous protocol, further algorithms are used to process the raw data in arriving at the particular pacing mode—AV configuration yielding optimum hemodynamic performance. If the maximum number of cc has been equaled or exceeded at 182 prior to the end of the assimilation of raw data, the protocol is again ended at 171 and the device restored to the permanent mode settings.

The algorithms used to process the accumulated raw data are found in FIGS. 7B–7D which are generally similar to those in FIGS. 3B–3E but do contain differences which will also be discussed.

Figure 7A:
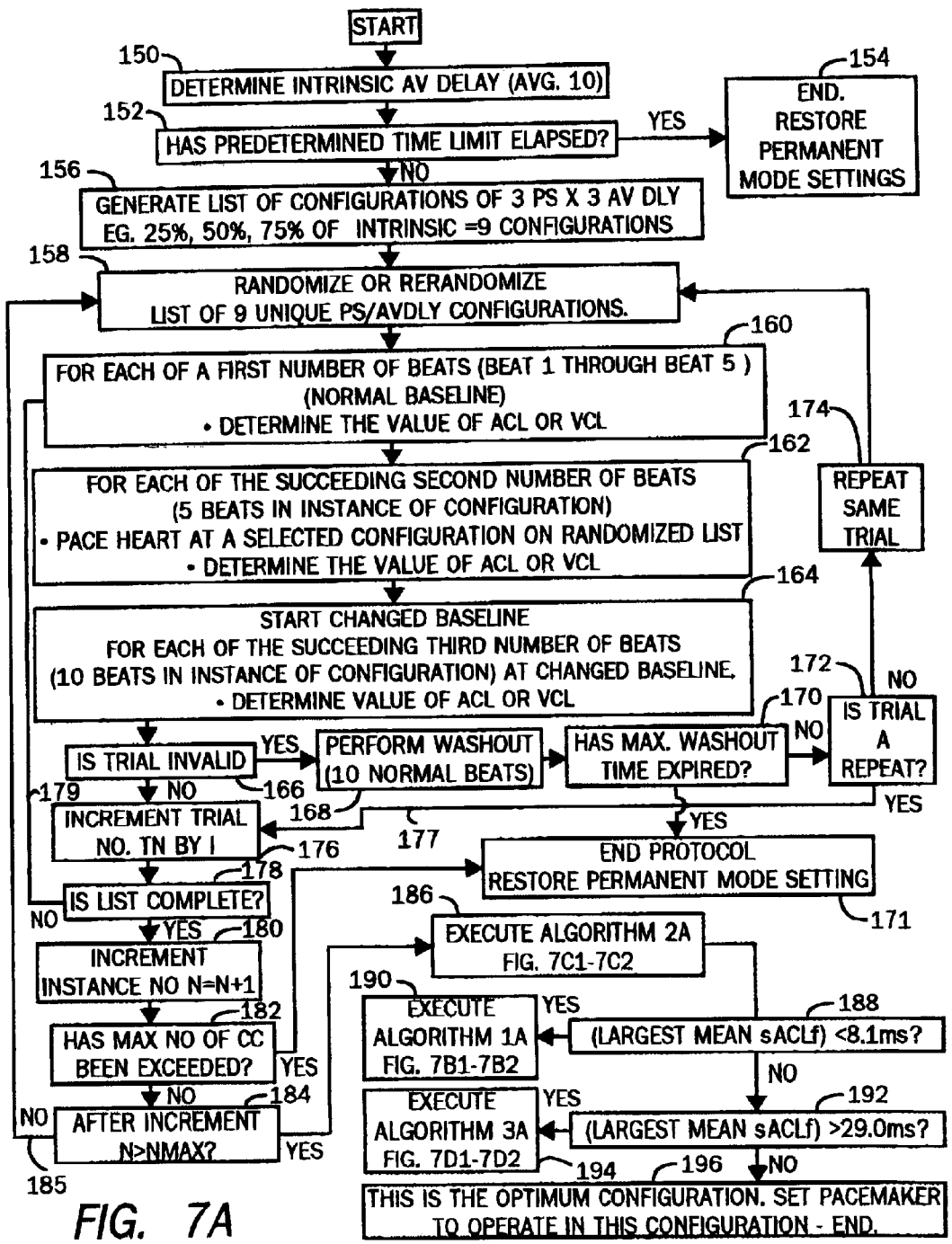

It should be noted in conjunction with FIG. 7A that when all of the configuration possibilities have been exhausted, the list of configurations or trials of 3 PS times 3 AV delays having been repeated 5 times, each time the list being re-randomized so that it is unlikely that the trials would occur in the same order in any two lists, the process moves to block 186. There algorithm 2A depicted in FIG. 7C, the basic optimization analysis algorithm 2A, is used to determine a candidate optimum configuration in much the same manner as algorithm 2 depicted in FIG. 3C. Blocks 188 and 192 are used to determine which further algorithm (blocks 190 and 194) is required for optimization or whether the candidate of algorithm 2A is, in fact, the optimum at 196.

Thus, in block 200, the raw ACL data (or VCL data) are first smoothed as in algorithm 2 using an 11 point moving Blackman window which yields a smooth ACL array (sACL) or smooth VCL array (sVCL). At block 202, data is checked for abnormal beats, the detection of which invalidates an instance or trial and at block 204, as in algorithm 2 (FIG. 3A), a determination is made from the 5 repetitions of each configuration as to whether less than 3 "valid trials" or "valid instances" occurred and, if so, the configuration is defined to be a "invalid configuration"; otherwise, if three or more "valid trials" or "valid instances" occur, it is defined to be a "valid configuration".

As seen in blocks 206 and 208, consistant with the philosophy of this protocol embodiment and unlike the embodiment of FIG. 3A, in order for the optimization protocol to continue, all configurations must be valid configurations, i.e., containing at least three out of five valid trials. Otherwise, the optimization determination is ended and the pacing device restored to the permanent mode settings. This provides an additional level of data screening to increase the reliability of the final outcome. This having been done, the ensuing blocks 210, 212, 214, 216 and 218 process the data in the same manner as blocks 80–90 of FIG. 3C. See also FIG. 9 as discussed below.

However, when the result of the outlier threshold test in box 216 determines, and with box 220, removes a MAX whose value is too large (relative to the median value) and this outcome, in turn, results in a particular configuration having less than three valid instances, this also makes the configuration invalid. The creation of an invalid configuration in this manner also results in ending the optimization protocol and a return to the permanent mode setting as shown in boxes 222 and 224. If the configuration remains valid at 222, it is returned to block 214 to again repeat steps 214 and 216 until such time as the outliers test set out in block 216 comes out true, producing the candidate optimum configuration at block 218.

When this occurs, as in the previous protocol with respect to FIG. 3A, reference is again made to FIG. 7A and box 188 where, after the candidate for the optimum configuration has been determined in FIG. 7C, further processing takes place to determine whether this or another candidate is the optimum configuration for pacemaker operation. As was the case in the previous protocol, specifically, a test is made at block 188 to determine whether the largest main sACLf is less than 8.1 milliseconds. If so, algorithm 1A of FIG. 7B, which is quite similar to algorithm 1 of FIG. 3B, is executed.

The first three steps 240, 242 and 244 perform the identical operations as the three blocks beginning with block 66 of FIG. 3B. It should be noted that here, consistent with this protocol, and as seen at blocks 246 and 248, a single invalid configuration will again end the optimization and restore the operation of the device to the permanent mode setting.

Figure 9:
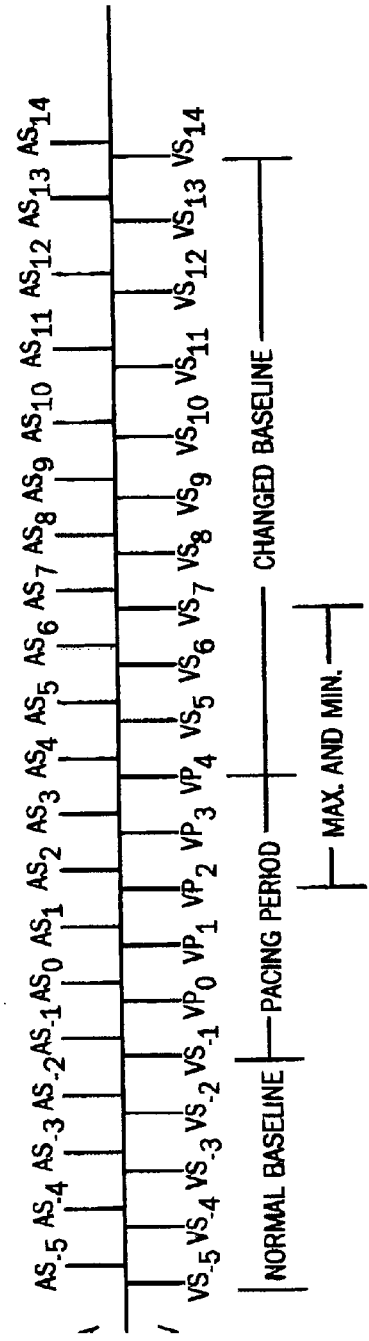
FIG. 9 is a representation of a series of baseline and paced beats useful in explaining the development of ACL features in accordance with the optimization algorithm of the alternate embodiment.
Figure 9:
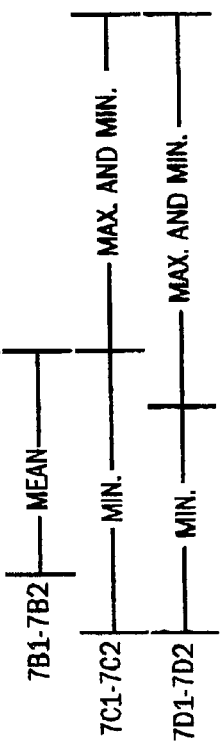

Next, as previously discussed with reference to block 67 in the flow diagram of FIG. 3B, is the block 250 which can be further explained in conjunction with FIG. 9, as was the case with block 67 in FIG. 3B, the maximum value and the minimum value of the smooth ACL in an interval from two beats after the first beat of the configuration instance to seven beats after the first beat of the configuration are computed. In this regard, FIG. 9 depicts a series of five baseline beats, followed by five paced beats of an instance or trial of a configuration, again followed by another series of ten changed baseline beats. The interval in which the maximum and minimum values of the smooth ACL's are to be located is labeled "MAX" and "MIN". They are represented for the three algorithms of FIGS. 7B, 7C and 7D. Likewise, the interval in which the mean value of the smooth ACL's is to be located is identified by "MEAN". Once the "MAX" and "MIN" values of sACL for the configuration instance are known, tests identical to those at 68 and 69 in block 67 are performed at 252 and 254 in block 250 of FIG. 7B.

As was the case in the first protocol and as indicated by blocks 70 and 71 of FIG. 3B, computation is made to determine the average or mean of the sACLf number of valid instances of that configuration at 256 and the particular valid configuration exhibiting the greatest mean of the smoothed ACL or VCL features is identified sACLf or sVCLf at 258. The pacemaker is then automatically programmed to operate with this optimum configuration.

As was the case with algorithm 1 of FIG. 3B, however, an optional sequence, including an outliers test may be performed in block 262 to remove a MAX whose value is too large (relative to the median values). Again, the empirically determined (predetermined threshold) of 9.5 may be used. If the result of this test is true, as shown at block 260, this is the optimum configuration that has been determined and the pacemaker can be set to operate at that configuration. However, if the test at block 262 proves false, the instance with the maximum value of sACLf or sVCLf is defined to be an invalid instance as is shown in block 264. If this once valid configuration now has less than three valid instances or trials at 265, then it is re-defined to be an invalid configuration which, according to this protocol, ends the optimization and restores the permanent mode setting at 266. If the configuration still has three or more valid instances, it remains valid and control then loops back over line 267 to block 258 to again repeat steps 258 and 262.

With reference again to FIG. 7A, it is seen that if the test at block 192 had established that the largest mean sCLf had been greater than 29.0 milliseconds, algorithm 3A, shown in FIG. 7D, would have been executed rather than algorithm 1A in FIG. 7B. We seen in FIG. 7D that the steps 280, 282, 284, 286 and 288 are substantially identical to the steps 200–208 in FIG. 7C and many of the steps in FIG. 7B except that in block 290 of FIG. 7D, the maximum value of sACL or sVCL is determined at an interval of from one beat after the first beat of a configuration instance rather than from two beats after a first beat of a configuration instance. (See FIG. 9) Blocks 292–304 are the same as blocks 212–224 of FIG. 7C with one notable exception. Block 304 of algorithm 3A shown in FIG. 7D differs from block 218 of algorithm 2A shown in FIG. 7C. Rather than identifying the candidate option configuration (FIG. 7C), the actual optimum configuration is established (FIG. 7D) and the pacemaker is then programmed to operate in this optimum configuration.

As was the case with the earlier protocol, the optimization of FIGS. 7A–7D is designed to be accomplished when the patient is asleep or otherwise in a sedentary state as was the case with FIG. 3E modifying FIG. 3A, FIG. 7A can also be modified by adding steps comparable to steps 49 and 50 of FIG. 3A in order to optimize the pacing of the same individual during physical activities. This being the case, it is believed unnecessary to add an entire new figure in this regard.

Thus, in accordance with the invention, patient tests have shown that the relatively easy-to-measure atrial cycle length (or ventricular cycle length) can be used to automatically determine the pacing mode and site-to-site delay configuration which provides pulse pressures greater than the pulse pressure achieved with baseline cardiac performance. The need for a special sensor to actually measure pulse pressure itself, which is difficult to measure, is eliminated.

In accordance with one aspect of the invention, and in addition to the above, it has been found that in bi-ventricular pacing dynamic inter-site delay adjustments may be made on a beat-by-beat basis based on a linear function of the VCL or ACL. This relationship may be represented by the relation:

$$d_{vv} = mi_{vv} + b$$

$$m = \frac{d_{max} - d_{min}}{i_{lrl} - i_{url}}$$

$$b = d_{max} - mi_{lrl}$$

where $i_{lrl}$ and $i_{url}$ are the lower and upper rate limit intervals, the lower and upper rate limits having been set by the physician;

$d_{max}$ and $d_{min}$ are the maximum and minimum interventricular delays for sequentially paced sites, one in each ventricle, which are also set by the physician based on the relative activity of the patient over time and which may be varied based on statistical activity trends of the patient;

$i_{vv}$ is the ACL (VCL could also be used);

$d_{vv}$ is the dynamic interventricular delay or the delay between sequentially paced sites, one in each ventricle.

Figure 6:
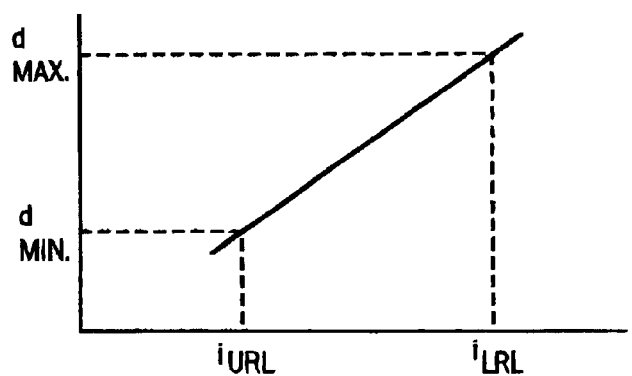
FIG. 6 is a plot of one dynamic delay v. cycle length relationship.

In this manner, the $d_{vv}$ inter-site delay can be caused to vary linearly with the ventricular cycle length (or ACL). This is illustrated by the plot of FIG. 6. Alternatively, it is contemplated that a non-linear function may be used.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. As already mentioned, the intrinsic and paced beat information can readily be telemetered out to an external programmer/monitor incorporating a microprocessor and associated memory so that the ACL determinations and signal processing thereof can be done external to the patient in arriving at the optimal pacing mode-AV delay interval. Hence, the scope of the invention is to be determined from the appended claims.

What is claimed is:

1. A method of optimizing the pacing mode and inter-site delay configuration of a dual chamber pacemaker of the type having means for sensing atrial depolarization events, means for sensing ventricular depolarization events and means for applying cardiac stimulating pulses selectively to the right, left or both ventricular chambers at a plurality of sites at predetermined delay intervals following detection of atrial depolarization events, comprising the steps of:

(a) determining a patient's intrinsic AV delay;

(b) generating randomized list of configurations, each having a specific pacing mode and AV delay, said AV delay being a function of the intrinsic AV delay;

(c) measuring a selected cardiac performance parameter selected from a group indicative of the performance of a patient's heart during multi-site pacing for a first number of beats to establish a baseline using a first setting comprising a first pacing mode and first inter-site delay interval;

(d) varying the setting in accordance with a configuration from step (b);

(e) measuring said parameter during pacing for a second number of beats;

(f) calculating and storing a performance parameter feature value obtained in steps (C) and (e);

(g) repeating steps (c)–(f) which define a trial until said randomizer list is exhausted;

(h) re-randomizing list of configurations in (b) a predetermined number of times (N) and repeating steps (c)–(g) for each randomization that each configuration is repeated for N trials;

(i) determining that data confirms that all configurations are valid and wherein any invalid configuration results in ending of the optimization and return of the pacemaker to permanent settings;

(j) determining an optimal inter-site delay interval and pacing mode configuration based on measurements of said parameter at said plurality of configuration, each having a plurality of trials; and (k) setting the inter-site delays and pacing mode configuration of the pacemaker to the optimal inter-site delays and pacing mode configuration established in step (j).

2. A method as in claim 1 wherein said selected cardiac parameter is selected from the group consisting of ACL and VCL.

3. A method as in claim 1 wherein said selected cardiac parameter is ACL.

4. A method as in claim 3 further comprising the step of performing a successful washout prior to repeating a trial.

5. A method as in claim 3 wherein any abnormal beats detected anywhere in a trial invalidate that trial.

6. A method as in claim 1 wherein a configuration is determined to be valid if a majority of trials of that configuration are valid.

7. A method as in claim 6 wherein said successful washout must occur within a fixed time limit otherwise the optimization is ended and permanent mode settings are restored.

8. A method as in claim 1 further comprising the steps of:

(1) testing the validity of each trial immediately after it is conducted; and (m) repeating an invalid trial once prior to conducting a different trial.

9. A method as in claim 1 further comprising the steps of:

(n) comparing the total number of cardiac cycles used in the optimization to a maximum allowable number and ending the optimization and restoring permanent mode settings if the number is exceeded.

10. A method as in claim 1 wherein the patient's AV delay is determined by averaging the delay over a predetermined number of normal beats and wherein that must be accomplished within a predetermined tine limit or the optimization ended and permanent mode settings restored.

11. A method as in claim 1 wherein the selected parameter is ACL and wherein a candidate optimum configuration setting is obtained by the following steps:

(o) smoothing the array of ACLs parameter values;

(p) determining for all instances of each pacing mode and inter-site delay configuration the maximum value of the smoothed ACLs in a first interval beginning after a change to the first number of beats $N_1$ and ending after a change to the second number of beats $N_2$ and a minimum value of the smoothed ACLs in a second interval beginning a predetermined number of beats prior to a change from the $N_2$ beats to the $N_1$ beats and ending with the beat associated with the maximum value;

(q) computing a smoothed ACL feature as the difference between the maximum value and the minimum value;

(r) calculating the mean value of the smoothed ACL features computed in step (h) over the all valid instances for each pacing mode inter-site delay configuration and determining the configuration yielding the largest mean value;

(s) determining among the valid instances associated with the configuration yielding the largest mean value a median value and a maximum value of smoothed ACL features.

12. A method as in claim 11 and when the ratio of maximum value and the median value of smoothed ACL features is greater than or equal to the predetermined threshold value, repeating steps (r) and (s) after recalculating the mean of the instances of the configuration associated with the largest mean value of smoothed ACL features after removing the instance having the maximum value of smoothed ACL features from the instances and if after removing the instance having the maximum value of smoothed ACL features from the instances this results in its configuration having less than a majority of valid instances, ending the optimization and restoring permanent mode settings.

13. A method as in claim 12 wherein said candidate optimum configuration is the optimum and the pacemaker is set to operate in that configuration.

14. A method as in claim 1 wherein the selected parameter is ACL and the feature value is calculated by the steps of:

(t) smoothing the array of ACLs;

(u) determining from the smoothed array of ACLs a maximum value and a minimum value in a first predetermined interval measured in beats for each inter-site delay and pacing mode configuration;

(v) determining from the smoothed array a mean value of ACLs in a second predetermined interval measured in beats for each inter-site delay and pacing mode configuration;

(w) computing an absolute value of the difference between said maximum value and said mean value and computing an absolute value of the difference between said minimum value and said mean value;

(x) comparing the absolute value of the difference between the maximum value and the mean value with the absolute value of the difference between the minimum value and the mean value to determine which is the larger;

(y) setting the ACL feature value to the difference between the maximum value and the mean value when the absolute value of that difference is greater than the absolute value of the difference between the minimum value and the mean value and setting the ACL feature value to the difference between the minimum value and the mean value when the absolute value of the difference between the maximum value and the mean value is less than or equal to the absolute value of the difference between the minimum value and the mean value;

(z) calculating the mean value of the smoothed ACL features computed in step (h) over the $N_3$ instances for each pacing mode inter-site delay configuration and determining the configuration yielding the largest mean value; and (aa) determining among the valid instances associated with the configuration yielding the largest mean value a median value and a maximum value of smoothed ACL features.

15. The method of claim 14 and when the ratio of maximum value and the median value of smoothed ACL features is greater than or equal to the predetermined threshold value, repeating steps (z) and (aa) after recalculating the mean of the instances of the configuration associated with the largest mean value of smoothed ACL features after removing the instance having the maximum value of smoothed ACL features from the instances and if after removing the instance having the maximum value of smoothed ACL features from the instances this results in its configuration having less than a majority of valid instances, ending the optimization and restoring permanent mode settings.

16. A method as in claim 1 wherein each configuration contains an AV delay in the range between 25% and 75% of intrinsic AV delay.

17. A method as in claim 1 wherein the selected parameter is VCL and wherein a candidate optimum configuration setting is obtained by the following steps:

(o) smoothing the array of VCLs parameter values;

(p) determining for all instances of each pacing mode and inter-site delay configuration the maximum value of the smoothed VCLs in a first interval beginning after a change to the first number of beats $N_1$ and ending after a change to the second number of beats $N_2$ and a minimum value of the smoothed VCLs in a second interval beginning a predetermined number of beats prior to a change from the $N_2$ beats to the $N_1$ beats and ending with the beat associated with the maximum value;

(q) computing a smoothed VCL feature as the difference between the maximum value and the minimum value;

(r) calculating the mean value of the smoothed VCL features computed in step (h) over the $N_3$ instances for each pacing mode inter-site delay configuration and determining the configuration yielding the largest mean value;

(s) determining among the valid instances associated with the configuration yielding the largest mean value a median value and a maximum value of smoothed VCL features.

18. A method as in claim 17 and when the ratio of maximum value and the median value of smoothed VCL features is greater than or equal to the predetermined threshold value, repeating steps (r) and (s) after recalculating the mean of the instances of the configuration associated with the largest mean value of smoothed VCL features after removing the instance having the maximum value of smoothed VCL features from the instances and if after removing the instance having the maximum value of smoothed VCL features from the instances this results in its configuration having less than a majority of valid instances, ending the optimization and restoring permanent mode settings.

19. A method as in claim 18 wherein said candidate optimum configuration is the optimum and the pacemaker is set to operate in that configuration.

20. A method as in claim 1 wherein the selected parameter is VCL and the feature value is calculated by the steps of:

(t) smoothing the array of VCLs;

(U) determining from the smoothed array of VCLs a maximum value and a minimum value in a first predetermined interval measured in beats for each inter-site delay and pacing mode configuration;

(v) determining from the smoothed array a mean value of VCLs in a second predetermined interval measured in beats for each inter-site delay and pacing mode configuration;

(w) computing an absolute value of the difference between said maximum value and said mean value and computing an absolute value of the difference between said minimum value and said mean value;

(x) comparing the absolute value of the difference between the maximum value and the mean value with the absolute value of the difference between the minimum value and the mean value to determine which is the larger;

(y) setting the VCL feature value to the difference between the maximum value and the mean value when the absolute value of that difference is greater than the absolute value of the difference between the minimum value and the mean value and setting the VCL feature value to the difference between the minimum value and the mean value when the absolute value of the difference between the maximum value and the mean value is less than or equal to the absolute value of the difference between the minimum value and the mean value;

(z) calculating the mean value of the smoothed VCL features computed in step (h) over the $N_3$ instances for each pacing mode inter-site delay configuration and determining the configuration yielding the largest mean value; and (aa) determining among the valid instances associated with the configuration yielding the largest mean value a median value and a maximum value of smoothed VCL features.

21. The method of claim 20 and when the ratio of maximum value and the median value of smoothed VCL features is greater than or equal to the predetermined threshold value, repeating steps (z) and (aa) after recalculating the mean of the instances of the configuration associated with the largest mean value of smoothed VCL features after removing the instance having the maximum value of smoothed VCL features from the instances and if after removing the instance having the maximum value of smoothed VCL features from the instances this results in its configuration having less than a majority of valid instances, ending the optimization and restoring permanent mode settings.

* * * * *